(12) United States Patent
Baron et al.

(10) Patent No.: US 10,768,156 B1
(45) Date of Patent: Sep. 8, 2020

(54) YIELD ANALYSIS THROUGH AGRONOMIC ANALYTICS

(71) Applicant: Farmer's Business Network, Inc., San Carlos, CA (US)

(72) Inventors: Charles B. Baron, Menlo Park, CA (US); Matthew Meisner, San Carlos, CA (US); Daniel Turkovich, San Francisco, CA (US)

(73) Assignee: Farmer's Business Network, Inc., San Carlos, CA (US)

( * ) Notice: Subject to any disclaimer, the term of this patent is extended or adjusted under 35 U.S.C. 154(b) by 977 days.

(21) Appl. No.: 14/746,769

(22) Filed: Jun. 22, 2015

Related U.S. Application Data

(60) Provisional application No. 62/069,152, filed on Oct. 27, 2014.

(51) Int. Cl.
*G01N 33/00* (2006.01)

(52) U.S. Cl.
CPC ................................ *G01N 33/0098* (2013.01)

(58) Field of Classification Search
CPC .............................. A01G 7/00; G01N 33/0098
USPC ........................................................ 702/189
See application file for complete search history.

(56) References Cited

U.S. PATENT DOCUMENTS

| 8,768,777 | B2 * | 7/2014 | Lin | ......................... | G06Q 10/08 |
| | | | | | 340/10.1 |
| 9,519,861 | B1 * | 12/2016 | Gates | ........................ | G06N 5/02 |
| 2003/0182144 | A1 * | 9/2003 | Pickett | .................... | G06Q 10/06 |
| | | | | | 705/317 |
| 2006/0282467 | A1 * | 12/2006 | Peterson | ................. | G06Q 50/02 |
| 2016/0066505 | A1 * | 3/2016 | Bakke | ..................... | G06Q 50/02 |
| | | | | | 700/275 |
| 2016/0078570 | A1 * | 3/2016 | Ethington | ........... | G06Q 10/1097 |
| | | | | | 705/7.21 |
| 2016/0290918 | A1 * | 10/2016 | Xu | .......................... | G01W 1/10 |

OTHER PUBLICATIONS

Agverdict, "Agverdict Combines Field-Specific Data With Our Agronomists' Knowledge," downloaded from http://www.agverdict.com/, 7 pgs. (document not dated, downloaded on Jun. 22, 2015).

(Continued)

*Primary Examiner* — Dzung Tran
(74) *Attorney, Agent, or Firm* — Klarquist Sparkman, LLP

(57) ABSTRACT

Yield analysis techniques are provided herein. The effect of various factors on yield are identified through agronomic analytics applied to many different types of data that can be collected by different farmers using different farming practices in different geographic areas. A yield analysis request for a crop type can be received. Based on aggregated crop data, a yield impact of one or more yield factors can be determined for the crop type. The aggregated crop data can be based on planting data and harvest data for a plurality of farm fields. The aggregated crop data can be determined in part by associating the planting data and harvest data for individual farm fields of the plurality of farm fields. A yield analysis can be provided for the crop type based on the yield impact of the yield factors. Farmers can adjust farming practices to achieve higher yield using the yield analysis.

19 Claims, 15 Drawing Sheets

(56) References Cited

OTHER PUBLICATIONS

Agverdict, "Scouting," downloaded from http://www.agverdict.com/services-1/, 8 pgs. (document not dated, downloaded on Jun. 22, 2015).
Hest, David, "Yield Pop offers new tools for comparing seed varieties," downloaded from http://farmindustrynews.com/electronics/yield-pop-offers-new-tools-comparing-seed-varieties, 3 pgs. (document not dated, downloaded on Jun. 22, 2015).
The Fertilizer Institute, "Implementing 4R Nutrient Stewardship on the Farm Right Now," downloaded from http://www.nutrientstewardship.com/sites/default/filges/images/T702-019901_4R_low%20rez_no%20crop.pdf, 2 pgs. (document not dated, downloaded on Jun. 22, 2015).
Yield Pop, "Yield Pop Partners with First," downloaded from http://www.agweb.com/article/yield_pop_partners_with_first_NAA_Ben_Potter/, 2 pgs. (document not dated, downloaded on Jun. 22, 2015).
The Climate Corporation, "ClimatePro Field-level insights powered by data science," downloaded from http://climate.com/climate-pro-for-your-farm/, 2 pgs. (document not dated, downloaded on Jun. 22, 2015).
The Climate Corporation, "Climate Basic," downloaded from https://climate.com/farm-data-with-climate-basic/, 2 pgs. (document not dated, downloaded on Jun. 22, 2015).
Precision Planting, "FieldView," downloaded from http://www.precisionplanting.com/#products/fieldview/, 5 pgs. (document not dated, downloaded on Jun. 22, 2015).
Field Scripts, "Unlock the Yield Potential in Your Fields," downloaded from http://www.fieldscripts.com/Pages/default.aspx?randomId=zbrorJUpTwwE8, 6 pgs. (document not dated, downloaded on Jun. 22, 2015).
Seed Matrix, "A Revolution in Advanced Seed Comparison Technology," downloaded from http://www.fieldscripts.com/Pages/default.aspx?randomId=zbrorJUpTwwE8, 6 pgs. (document not dated, downloaded on Jun. 22, 2015).
Specter, Michael, "Climate by Numbers," *The New Yorker*, Nov. 11, 2013, downloaded from http://www.newyorker.com/magazine/2013/11/11/climate-by-numbers, 14 pages.
Seed Matrix, "How it Works," downloaded from https://seedmatrix.com/how-it-works.html, 2 pgs. (document not dated, downloaded on Jun. 22, 2015).
First, "Corn Grain, Corn Silage & Soybean Crop Harvest Reports," downloaded from http://firstseedtests.com/, 1 pg. (document not dated, downloaded on Jun. 22, 15).
First, "Corn Grain, Corn Silage & Soybean Crop Harvest Reports," downloaded from http://firstseedtests.com/, 1 pg. (document not dated, downloaded on Jun. 22, 2015).
First, "FAQs," downloaded from http://firstseedtests.com/faq.shtml, 2 pgs. (document not dated, downloaded on Jun. 22, 2015).
The Ohio State University Extension, "Agronomic Crops Network," downloaded from http://agcrops.osu.edu/, 2 pgs. (document not dated, downloaded on Jun. 22, 2015).
Grassi, Matthew J., "Agronomic Crops Network," downloaded from http://www.precisionag.com/data/the-climate-corp-launches-climate-basic-climate-pro-for-2014/, 4 pgs. (document not dated, downloaded on Jun. 22, 2015).
Seedmatrix, "SeedMatrix Revolutionizes Variety/Hybrid Data Management," downloaded from https://seedmatrix.com/press.html, 1 pg. (document not dated, downloaded on Jun. 22, 2015).

\* cited by examiner

YIELD ANALYSIS THROUGH AGRONOMIC ANALYTICS

CROSS REFERENCE TO RELATED APPLICATION

This application claims the benefit of U.S. provisional application 62/069,152, filed Oct. 27, 2014 and titled "AGRONOMIC WEB PORTAL," which is incorporated herein by reference in its entirety.

FIELD

This application relates to advances in agronomic technology.

BACKGROUND

Agriculture has become increasingly dependent upon technology in recent years. Planting equipment and harvesting equipment are now commonly equipped with monitors, sensors, and other instrumentation that allow farmers to record farming activity with fine granularity. Such data allows farmers to make better decisions regarding farming practices and to accurately see the results of these decisions. Although myriad data can be gathered, analysis and use of the data is typically left to the farmer for the farmer's sole benefit.

SUMMARY

Examples described herein relate to achieving higher crop yield by using agronomic analytics to perform a yield analysis for a crop type. In the described examples, a yield analysis request for a crop type can be received. Based on aggregated crop data, a yield impact of one or more yield factors can be determined for the crop type. The aggregated crop data can be based on planting data and harvest data for a plurality of farm fields. The aggregated crop data can be determined in part by associating the planting data and harvest data for individual farm fields of the plurality of farm fields. A yield analysis can be provided for the crop type based on the yield impact of the yield factors.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

The foregoing and other objects, features, and advantages of the claimed subject matter will become more apparent from the following detailed description, which proceeds with reference to the accompanying figures.

DETAILED DESCRIPTION

Using the systems, methods, and computer-readable media described herein, a yield analysis can be provided that indicates the impact of various factors on crop yield. Farmers can use this information to make planting choices (e.g., seed variety, row spacing, etc.) or post-planting choices (e.g., irrigation, fertilizer/pesticide application, etc.) that result in higher yield.

The yield analysis is based on agronomic analytics applied to many different types of data that can be collected by different farmers using different farming practices and/or in different geographic areas. Data can be collected, for example, for hundreds or thousands of farm fields and for multiple years. Analyzed data can include planting data, harvest data, weather data, soil type, farming practice data (e.g., fertilizer application, pesticide application, irrigation data, till status, etc.), and other data.

By analyzing yield over such wide-ranging conditions, an in-depth understanding of yield, and the factors that affect yield, can be established. For example, the relative contribution to yield of a variety of factors can be determined (e.g., contribution to variability in yield among fields when other factors are controlled for). The relative contributions of different factors can be expressed, for example, as a statistical relationship, and can be determined, for example, for particular crops, seed varieties, regions, and/or years. Changes in yield corresponding to changes in various factors can also be determined. As an example, changes in yield that result from changes in row spacing can be determined. Examples are described in detail below with reference to FIGS. 1-15.

Figure 1:
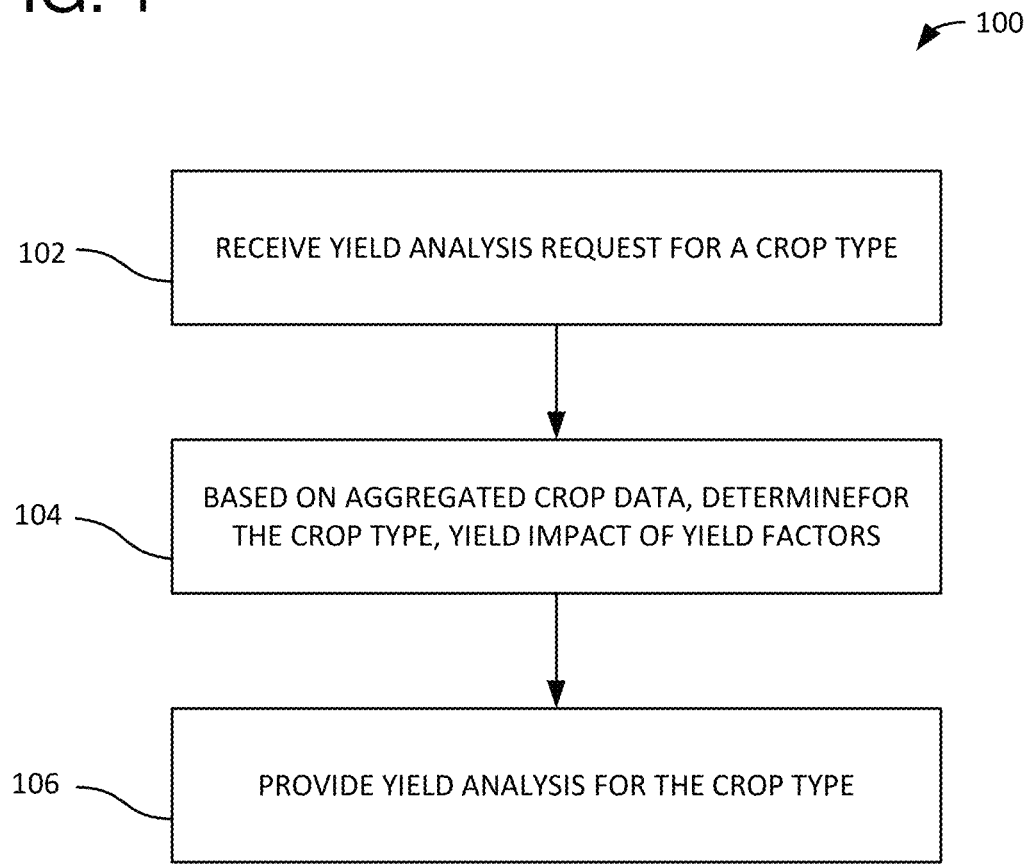
FIG. 1 illustrates an example method for providing a yield analysis for a crop type.

FIG. 1 illustrates an example method 100 for providing a yield analysis for a crop type. In process block 102, a yield analysis request for a crop type is received. The request can specify one or more constraints to be used in the yield analysis. Constraints can include: a crop; a seed variety; a farm field, county, state, or other region; or other factor. The request can also specify farm field information representing a farm field or fields for which yield analysis is requested. Farm field information can include, for example: a county, state, or other geographic region of the farm field; latitude and longitude of a point within the farm field; boundaries of the farm field; or one or more soil types of the farm field.

Farm field information can also be in the form of a shapefile, geodatabase, or other geospatial file indicating boundaries of the farm field and/or boundaries of subdivisions within the farm field. In examples where the farm field information includes location information, soil type databases, such as Soil Survey Geographic Database (SSURGO) data, can be accessed to identify one or more soil types that correspond to the location information. SSURGO data can also provide, for example, soil texture classification, drainage quality, slope, sand/silt/clay percentages, estimated productivity, pH, and other information that can also be associated with a farm field. Farmers can also have a soil analysis performed on various levels of granularity to identify soil nutrients, pH, composition, etc. In some examples, the request is received through an agronomic web portal.

In process block 104, based on aggregated crop data, a yield impact of one or more yield factors is determined for the crop type. Yield factors can include, for example, at least one of: seed variety, soil type, precipitation, planting speed, row spacing, seed spacing, seeding rate, planting depth, crop rotation, tillage, irrigation, fertilizer application, pesticide application, or weather events. Yield impact can include, for example: (i) a yield corresponding to values for a yield factor and/or (ii) a change in yield corresponding to values for a yield factors. Yield impact can be provided, for example, as ranges of yield or change in yield. The ranges can indicate a confidence in the corresponding yield factor's impact on yield or change in yield that can be based on statistical quantifications of uncertainty.

The aggregated crop data is based on planting data and harvest data for a plurality of farm fields. In some examples, at least some of the planting data are acquired using planter-mounted sensors, and at least some of the harvest data are acquired using harvester-mounted sensors. The aggregated crop data is determined in part by associating planting data and harvest data for respective farm fields of the plurality of farm fields. Association of planting data and harvest data is discussed in greater detail below with respect to FIGS. 2, 6, 8, and 9, for example.

Planting data can include planting points as well as data that correspond to the planting points. For example, at a planting point, one or more seeds are planted of a certain seed variety, at a particular row spacing, planting depth, etc. Planting data can comprise, for example, at least one of: seed variety, planting rate, seeding rate, planter type, row spacing, intra-row spacing (seed spacing), planting depth, or latitude and longitude of planting points. A "planter" as used herein refers to any machinery used to plant seeds and includes seed drills, seeders, planters (including planters towed behind tractors), crop-specific planters, and other machines for planting.

Similar to planting data, harvest data can include harvest points as well as data that correspond to the respective harvest points, such as an amount of crop harvested. Harvest data can comprise, for example, at least one of: latitude and longitude of harvest points, amount of crop harvested, moisture content of crop harvested, or harvester type. Harvest data can be used to determine yield, which is an amount of crop harvested per unit area. For example, the yield for a farm field can be determined by adding the amount of crop harvested at each harvest point within a field and dividing by the area of the field. A "harvester" as used herein refers to any machinery used to harvest crops and includes combine harvesters (combines), forage harvesters, crop-specific harvesters, and other machines for harvesting.

The aggregated crop data can also be based on at least one of: weather event data, fertilizer application data, or pesticide application data for at least some of the plurality of farm fields. Weather event data can include a number or timing of severe weather events, an amount of precipitation for a duration of time (e.g., for a number of weeks after planting, for a season, etc.), a number of days with/without precipitation, temperature data, etc. The aggregated crop data can be aggregated, for example, by combinations of soil type and seed variety. In some examples, crop data is aggregated according to additional or other data category combinations. For example, crop data can be aggregated based on combinations of soil type, seed variety, and row spacing; seed variety and precipitation; etc.

Crop data can be aggregated first on a field level, to create a field-level data summary, and then, in some examples, field-level data summaries for many different fields can be aggregated. In some examples, agronomic analytics are applied to the field-level data summaries. Data representing many fields covers a range of conditions—different soil/land characteristics, geographic areas, different years, and different climatic conditions—that allows estimation through agronomic analytics of, for example, expected performance of different seed varieties and expected effects of various factors on crop yield. The expansive data used provide high statistical confidence and relevance for the wide range of conditions that may be encountered in the future in agricultural systems.

In process block 106, a yield analysis is provided for the crop type. The yield analysis is based on the yield impact of the one or more yield factors. The yield analysis can include an indication of the yield impact of a yield factor. For example, the yield analysis can include a graphical representation depicting yield or a change in yield corresponding to values for the yield factor. This can take the form of a two-dimensional plot of values for a yield factor on the x-axis and yield or change in yield on the y-axis. A curve shown by the plot can also include a statistical confidence interval (e.g., one standard deviation above/below). In some examples, the yield analysis includes an indication of a contribution of one or more yield factors to yield. (E.g., a contribution to variability in yield after controlling for other factors.) This can take the form of, for example, a bar graph or list illustrating a relative contribution of various factors (e.g., corn yield is determined 53% by variety, 10% by soil type, etc.). The yield analysis can be converted into a mobile-device-friendly visual arrangement and transmitted to a farmer mobile device.

Method 100 can also comprise providing a recommendation of a seed variety to plant, farming practices to follow, etc. Method 100 can further comprise planting a recommended seed variety or performing a recommended farming practice. Method 100 can also comprise transmitting a farming practice instruction or change to a farm equipment computer, farmer mobile device, or other computing device to update settings or values on the farm equipment. For example, a seeding rate or seed spacing determined based on the yield analysis can be transmitted wirelessly or through a wired connection to a computerized control system of a planter. When the planter is operated, seeds are planted according to the seeding rate or seed spacing.

Figure 2:
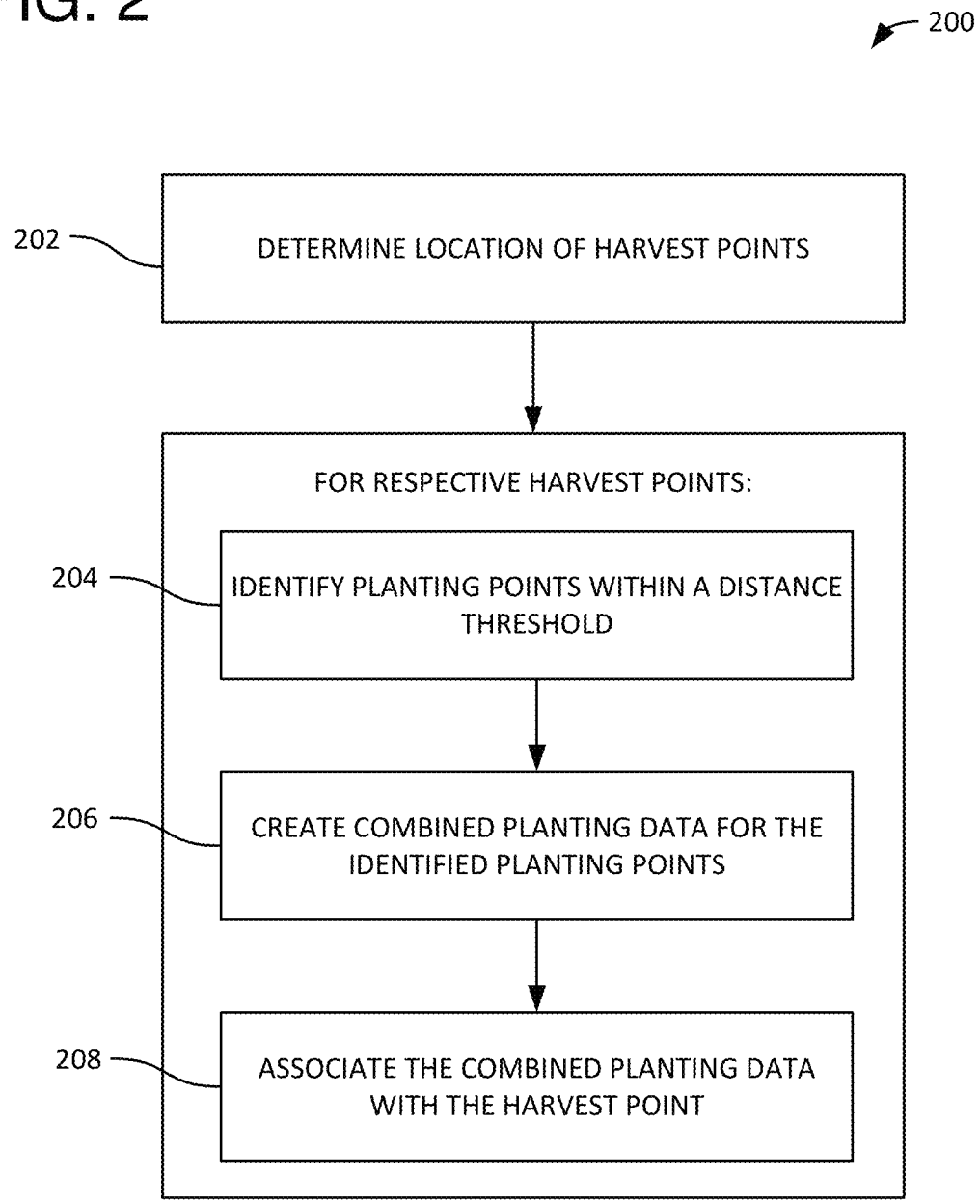
FIG. 2 illustrates an example method for associating planting points and harvest points.

The locations of planting points and harvest points typically do not correspond exactly, so in order to analyze the impact of the planting practices represented by planting data, fertilizer applications, pesticide applications, etc. on yield, planting data and other data are associated with harvest data. Planting data may include some information not present in the harvest data (and vice-versa). For example, harvest data may not include the seed variety type, but the seed variety type can be obtained from the associated planting data. FIG. 2 illustrates a method 200 of associating planting data and harvest data for a farm field. In process block 202, locations are determined for a plurality of harvest points. Locations can be acquired using positioning system sensors, such as a GPS receiver, mounted on, integrated into, or otherwise associated with a harvester. Latitude and longitude coordinates for harvest point locations can be recorded and stored in local memory or wirelessly transmitted to cloud or other storage.

Process blocks 204, 206 and 208 are performed for the individual harvest points. In process block 204, one or more planting points are identified that are within a distance threshold from the harvest point. The distance threshold can be fixed or set by a user and adjusted as needed to increase accuracy. The distance threshold is used to set a limit past which a planting point is unlikely to have resulted in a harvest point. For example, it might be considered to be unlikely that a seed planted 100 feet away from a harvest point is a seed that grew into the crop harvested at the harvest point. Example distance thresholds include three feet, four feet, five feet, 10 feet, 20 feet, etc. In some examples, only planting points that are both within the distance threshold from the harvest point and that have a seed variety that matches the crop type or seed variety of the harvest point are identified as being within the threshold. This helps limit the harvesting of one crop type or variety from being associated with seeds planted of a different crop type or variety. In some examples, the number of planting points associated with a harvest point can be user-selectable. For example, if a user sets a threshold of five planting points to one harvest point, the five planting points closest to the harvest point are associated with the harvest point even if more than five planting points are within the threshold.

In some cases, it can occur that no planting points are within a threshold from a harvest point. The data from the harvest point can still be used to determine a more accurate understanding of yield associated with a seed variety, but this harvest data may not be associated with other information such as planting speed and seeding rate that are typically included in planting data and thus may not be used in the analysis of the effect of such variables on yield.

In process block 206, combined planting data is created for the one or more planting points within the distance threshold. Combined planting data can be created in a number of ways, including averaging (e.g., a weighted or unweighted average) the planting data of the planting points within the distance threshold. In a weighted average example, combined planting data can be created by determining a weighted average of at least some planting data for the one or more planting points based on a distance of the respective planting points from the harvest point. For example, an inverse weighting can be used in which planting data for planting points nearer to the harvest point are given more weight than planting data corresponding to planting points farther away from the harvest point. In this way, weight is apportioned based on a likelihood that the planting points do actually correspond to the harvest point. Different types of planting data can be combined differently. For example, some types of planting data can be averaged, and for other types of planting data, a most common value (median) can be used.

However the combined planting data is created, the combined planting data represents the characteristics of planting points that likely resulted in the harvest observed at a harvest point. In process block 208, the combined planting data is associated with the harvest point. The harvest points can be stored, for example, in a geospatial file such as a shapefile, where locations (e.g., latitude/longitude) of harvest points are rows and harvest data (e.g., amount harvested) are stored in columns. Combined planting data for respective harvest points can be added as additional columns. The result of method 200 is that harvest points are now associated not only with other harvest data but with planting points and/or planting data, allowing relationships to be understood regarding certain planting data that result in certain harvest data.

The information associated with the individual harvest points can then be aggregated to form a field-level data summary representing the physical growth of one or more crops on the farm field. For example, the harvest points can be examined, and different (e.g., unique or distinct) seed-variety-and-soil-type combinations (or other data type combinations) of the harvest points can be identified. In some examples, soil sub-types or similar soil types can be considered a same type for the purposes of forming seed-variety-and-soil-type combinations, and/or similar seed varieties can be considered a same variety. Data associated with harvest points can then be aggregated according to the combinations. An example result for a farm field after such a process is a field-level data summary indicating all of the different soil-type-and-seed-variety combinations of the harvest points in the farm field (e.g., four unique combinations), and for each combination, averaged or otherwise combined data (e.g., yield). Field-level data summaries can be aggregated for many different fields (e.g. hundreds, thousands, or tens of thousands of fields), and agronomic analytics can be used to identify the contribution of various factors to yield. In some examples, data in field-level data summaries are aggregated by averaging results for each soil-type-and-seed-variety combination. For example, for 50 different farm fields that each planted a same seed variety in a same soil type, yield data for the 50 fields can be averaged. A weighted average can be used such that the contribution of data for each of the farm fields of the 50 farm fields corresponds to the relative acreage of the fields relative to the total acreage of the 50 fields.

Although the association of planting and harvest data is discussed in this document as associating planting data with harvest points, harvest data can also or alternatively be associated with planting points. In such an approach, an amount of crop harvested at harvest points within a threshold from respective planting points are combined to determine the yield at the planting point. Some harvest points may not be associated with planting points, and harvest data for these points can be omitted or can be associated with the nearest planting point, even if the harvest point is beyond a threshold from the planting point.

Figure 3:
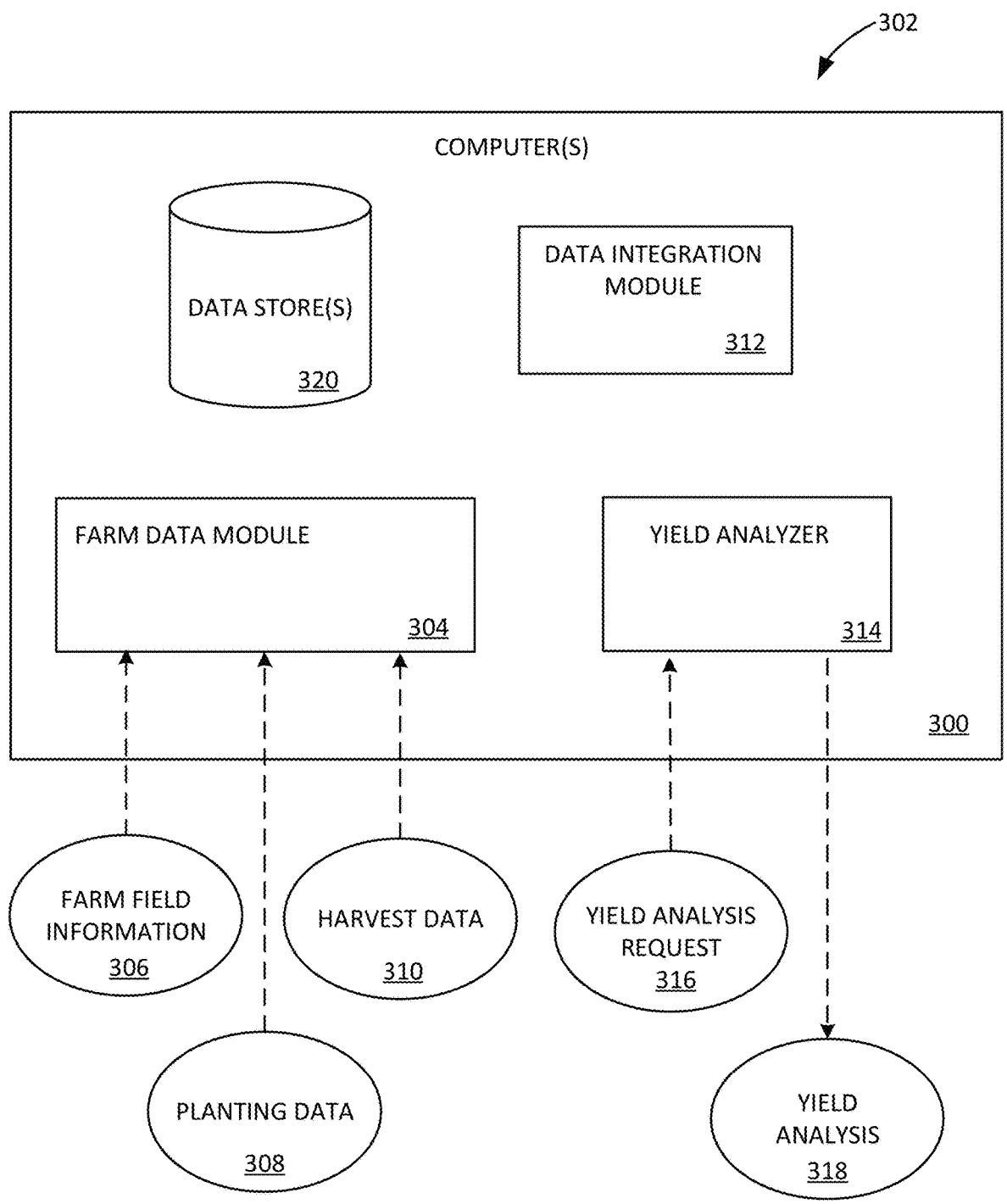
FIG. 3 illustrates an example analytics-based yield analysis system.

FIG. 3 illustrates one or more computers 300 implementing a system 302. Computer(s) 300 include a processor and a memory (not shown) and can be server computers, client computers, a group of distributed computers, or other computers. System 302 includes farm data module 304. Farm data module 304 is configured to receive farm field information 306, planting data 308, and harvest data 310 for a plurality of farm fields. Examples of data that can be included in farm field information 306, planting data 308, and harvest data 310 are discussed above with respect to FIG. 1. Farm data module 304 can also be configured to receive farming practice data (e.g., tillage status, crop rotation data, fertilizer application, pesticide application, irrigation, etc.), weather data, soil type data, or other data related to the conditions of the farm field, or environmental conditions near the farm field.

Returning to FIG. 3, a data integration module 312 is configured to create, for the respective farm fields of the plurality of farm fields, a field-level data summary representing the physical growth of one or more crops on the farm field. The field-level data summary is created in part by associating planting data and harvest data for the farm field. Associating the planting data and the harvest data can include, for example, determining a latitude and a longitude for a plurality of harvest points in the harvest data and determining a latitude and a longitude for a plurality of planting points in the planting data. For the respective harvest points: one or more of the plurality of planting points can be identified that are (i) of a same seed variety as a harvest point and (ii) within a distance threshold from the harvest point; combined planting data can be created for the one or more planting points within the distance threshold; and the combined planting data can be associated with the harvest point.

Data integration module 312 can be further configured to create the field-level data summary by associating a soil type with the respective harvest points. The soil type can be retrieved from a soil type database such as SSURGO or can be provided in farm field information 306. For the plurality of harvest points, combinations (e.g., unique or distinct combinations) of (i) associated seed variety and (ii) associated soil type can be determined. For the respective unique combinations, harvest points associated with the combination can be identified, and at least some of the planting data and harvest data associated with the identified harvest points can be combined. Combinations of other data types can also be created. Field-level data summaries can also be growing-season specific. For example, if two crops are planted in a field during two different growing seasons. A field-level data summary can be created for each growing season.

System 302 can also include a data aggregator (not shown) that is configured to combine the field-level data summaries for the plurality of farm fields created by data integration module 312 into aggregated crop data. The aggregated crop data can be aggregated, for example, in accordance with the unique combinations of (i) associated seed variety and (ii) associated soil type in the field-level summaries. For example, the data aggregator can average or otherwise combine the yield for specific soil-type-and-seed-variety combinations of the field-level data summaries. As an example, a county, state, regional, or agronomic network-wide average yield for a particular soil-type-and-seed-variety combination can be determined. The data aggregator can determine the aggregated crop data on-demand (e.g., upon receiving a request from a user to provide a seed variety recommendation for a particular field and crop). The data aggregator can also aggregate data independent of receiving a request from a user and update the aggregated data periodically or upon receipt of new field-level summaries.

In some examples, the data aggregator is omitted, and the "aggregated crop data" comprises the field-level summaries (which are formed by aggregating data at a field-level by data integration module 312) for the plurality of farm fields. For example, statistical techniques can be applied to combinations of the field-level data summaries rather than aggregations of the field-level data summaries (e.g., many field-level data summaries can be statistically analyzed rather than analyzing a compression of many field-level data summaries into a single aggregation). For example, a field may have 10 unique soil-type/seed variety combinations (and therefore 10 corresponding aggregations of planting, harvest, weather, and/or other data), while a second field may have 20 such combinations and aggregations. To analyze the data that represents the first and second fields, statistical modeling can be performed on the combination of the data (i.e., on the 30 soil-type/seed variety combinations over which data was aggregated for one field or the other). In some examples, however, some additional aggregation is performed.

A yield analyzer 314 is configured to receive a yield analysis request 316 for a crop type. Yield analyzer 314 is configured to determine crop-specific yield impacts of one or more yield factors based on the field-level data summaries created by data integration module 312. Yield factors can include, for example, at least one of: seed variety, soil type, precipitation, planting speed, row spacing, seed spacing, seeding rate, planting depth, crop rotation, tillage, irrigation, fertilizer application, pesticide application, or weather events. A crop-specific yield impact can include, for example: (i) a yield corresponding to values for a yield factor and/or (ii) a change in yield corresponding to values for a yield factors.

Figure 10:
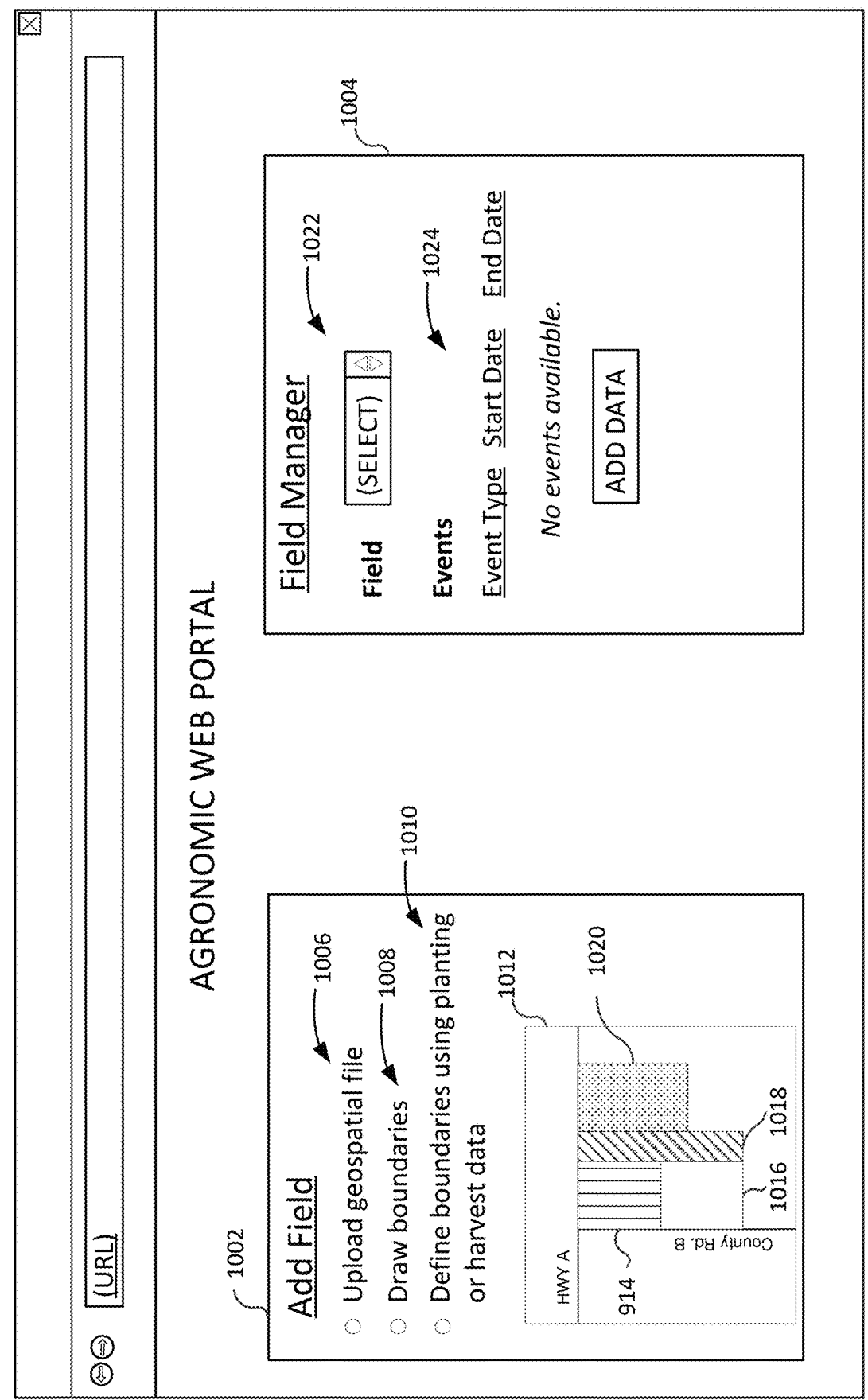
FIG. 10 illustrates an example agronomic web portal including add field and field manager functionality.
Figure 11:
FIG. 11 illustrates an example agronomic web portal including yield analysis, analyze my operation, and seed finder functionality.
Figure 12:
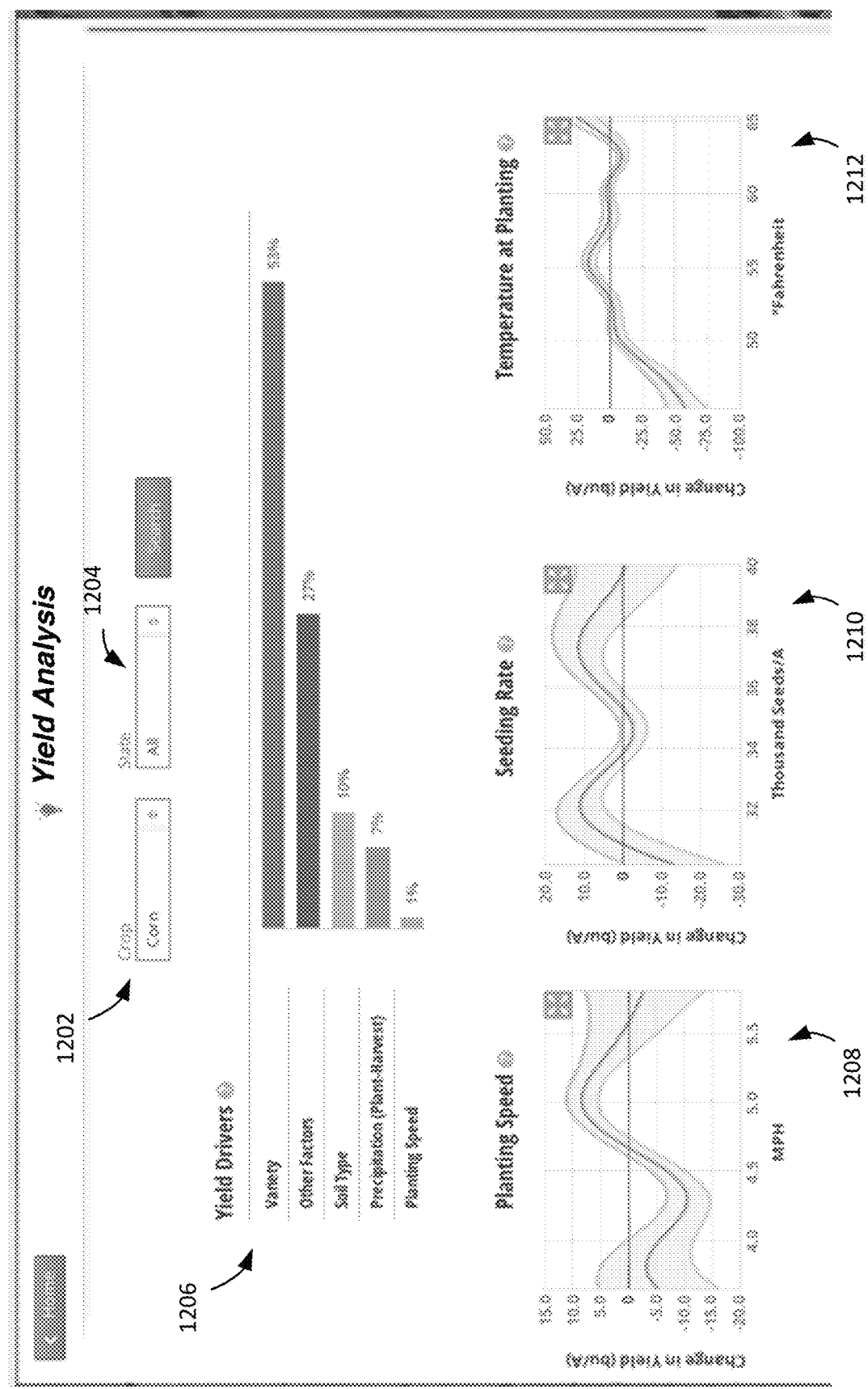
FIG. 12 illustrates a yield analysis interface showing yield drivers and yield impact plots.

Based on the crop-specific yield impacts of the one or more yield factors, yield analyzer 314 is configured to provide a yield analysis 318 for the crop type. Yield analysis 318 can include, for example, at least one of: yield corresponding to values for the one or more yield factors; change in yield corresponding to values for the one or more yield factors; or an indication of a contribution of at least one of the one or more yield factors to yield. Yield analyzer 314 can be further configured to provide a recommendation of at least one of: a seed variety, a planting practice, a fertilizer application practice, a pesticide application practice, or an irrigation practice. In some examples, yield analyzer 314 can provide an estimate yield or estimated yield range that are likely to occur for a given set of growing conditions and crop management practices. Yield analyzer 314 can also be configured to receive the request for a yield analysis through a web portal. This is illustrated in FIGS. 10-12.

Farm field information 306, planting data 308, harvest data 310, field-level data summaries, and aggregated crop data can be stored in data store(s) 320. Data store(s) 320 can be, for example, distributed, local to computer(s) 300, accessible to computer(s) 300 over a network, and/or in the cloud. The various components of system 302 can each be in communication with each other.

Figure 4:
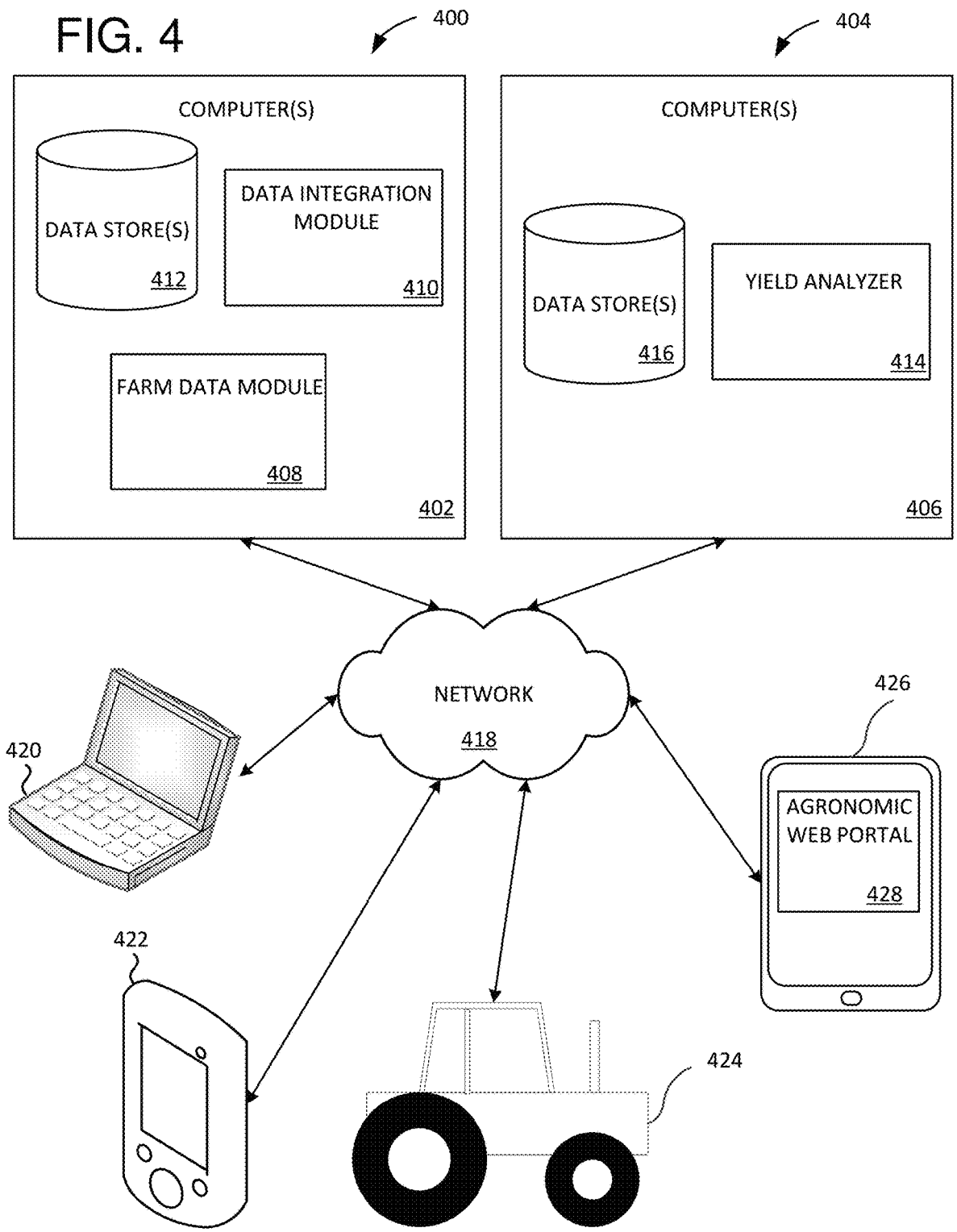
FIG. 4 illustrates an example analytics-based yield analysis system and various devices in communication with the system over a network.

FIG. 4 illustrates an example in which functionality similar to the functionality of system 302 of FIG. 3 is subdivided into a first subsystem 400, implemented by first computer(s) 402 and a second subsystem 404, implemented by second computer(s) 406. First subsystem 400 includes a farm data module 408, a data integration module 410, and a data store(s) 412. The functionality of farm data module 408 and data integration module 410 can be similar to the corresponding modules shown in FIG. 3. Second subsystem 404 includes yield analyzer 414 and data store(s) 416. The functionality of yield analyzer 414 can be similar to the corresponding modules shown in FIG. 3.

First computer(s) 402 and second computer(s) 406 are connected wired or wirelessly to network 418. Network 418 can be the Internet, a local area network (LAN), a wireless local area network (WLAN), a wide area network (WAN), or other type of network, wired or wireless. Farmer computer 420, farmer mobile device 422 (e.g., a tablet or smart phone), or farm machinery 424 (e.g., a planter or harvester) can be connected to network 418 and can provide farm field information, planting data, and/or harvest data to farm data module 408 via network 418. Farmer computing device 426 can be used to access the functionality of yield analyzer 414 via agronomic web portal 428 and network 418. Agronomic web portal 428 can also be used to provide farmer data from farmer computer 420, farmer mobile device 422, or farm machinery 424. Examples of agronomic web portal 428 are shown in FIGS. 10-12.

As shown in FIG. 4, different farmers in various geographic regions can provide farm field information, planting data, and/or harvest data through network 420, and this information can be used to inform yield analyzer 414. A farmer can then submit a yield analysis request through agronomic web portal 428, which accesses yield analyzer 414 and returns a yield analysis. Although farmers who provide data to inform yield analyzer 414 can also submit requests for a yield analysis, farmers can submit yield analysis requests without providing data other than farm field information, or even without providing any information.

Figure 5:
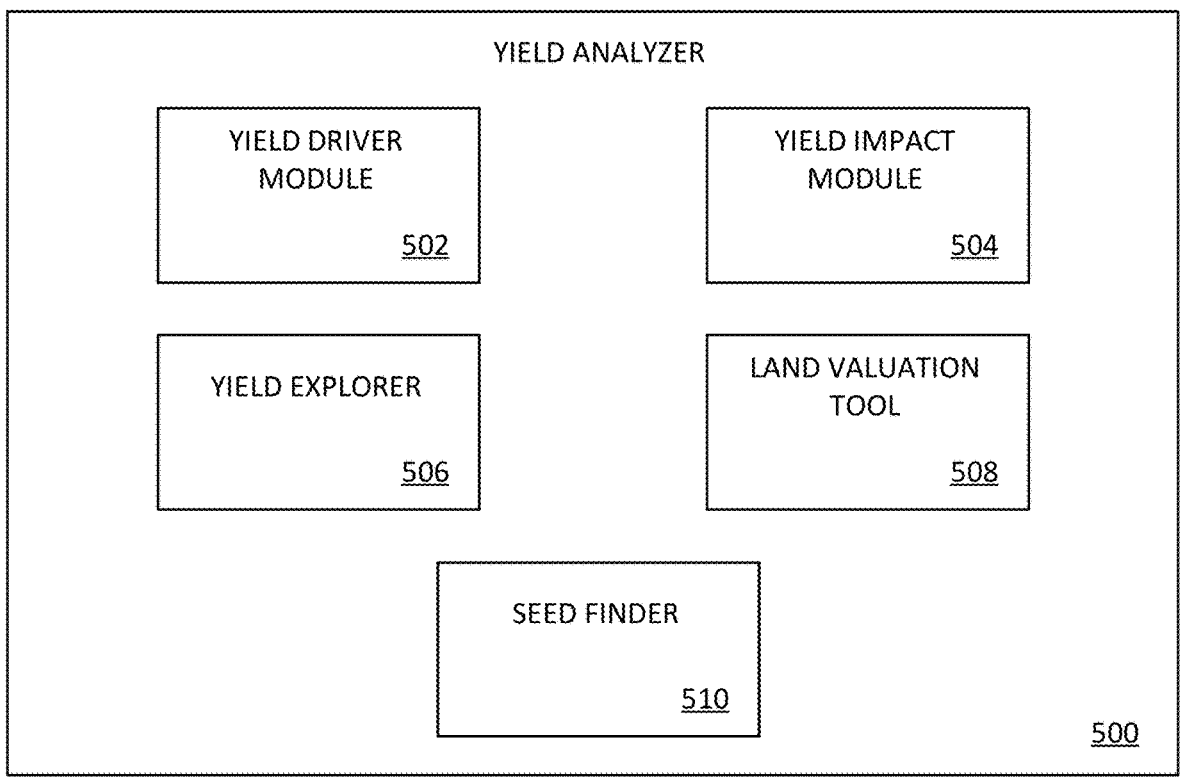
FIG. 5 illustrates an example yield analyzer.

FIG. 5 illustrates a yield analyzer 500. Yield analyzer 500 includes a yield driver module 502. Yield driver module 502 is configured to determine a contribution of one or more yield factors to yield. Yield factors that contribute to a variability in yield for a region are "yield drivers," although this term does not necessary imply causation. That is, from a statistical perspective, differences in yield are associated with different values of a yield factor. This can be thought of as a yield factor that, for different values of the yield factor (e.g., different seed variety, different row spacing, etc.), "drives" or affects yield. Yield driver module 502, for example, might determine that for corn in the state of Nebraska, variability in yield over different farm fields that has been recorded is 40% accounted for by the choice of seed variety, 10% by soil type, 5% by row spacing, etc. Yield drivers thus indicate to a farmer which factors have a greater influence on yield. If a farmer has limited time or money, yield drivers indicate the yield factors on which the farmer can best allocate resources (e.g., selecting a higher-yielding seed variety as opposed to altering row spacing, irrigation, etc.).

A yield impact module 504 is configured to determine yield impacts—that is, how yield changes when a yield factor changes. Yield impacts can be provided, for example, as (i) a yield corresponding to values for the one or more yield factors or (ii) a change in yield corresponding to values for the one or more yield factors. Example graphical indications of yield impacts are illustrated in FIG. 12.

Yield drivers can be determined based on yield impacts for different factors. For example, the impact of planting speed, row spacing, temperature at planting, etc. on yield for different seed varieties of corn can be determined and analyzed to determine how much of the variability among the yield of the different seed varieties is associated with the individual factors (planting speed, row spacing, temperature at planting, etc.).

A yield explorer 506 is configured to allow a user to select one or more various yield factors along with one or more geographic areas. For example, a user can select options to view how row spacing affects corn yield and/or soybean yield in two different states. Using yield explorer 506, a user can select various filters (such as state, county, soil texture, year, etc.) and a yield factor of interest. Yield explorer 506 then provides an analysis (e.g., a data visualization or text) estimating the yield impacts of various values for the yield factor of interest for the conditions selected using the filters. In some examples, yield explorer 506 allows a user to specify a seed variety as well as year(s), state(s), soil texture(s), crop rotation practice(s), or other information. The provided analysis can then include estimated yield and yield impacts, specific to the year(s), state(s), soil texture(s), crop rotation practice(s), or other information, for a number of yield factors (e.g. 10 yield factors). The yield factors and number of yield factors for which the analysis is provided can be predetermined or user selected.

Yield analyzer 500 can also include a land valuation tool 508. Land valuation tool 508 can receive a farm field ID (e.g., for a field associated with a user's account), a geospatial file for a farm field, user input to define boundaries, or other location information to indicate an area for which a valuation is desired. Characteristics of the land can be accessed, for example, from data associated with the farm field ID, from soil type databases, from historical weather data for a field, or from other sources, and yield impacts of various factors can be determined. A crop price and expected yield can be used to determine a land valuation. As an example, a farmer can select one or more parcels of land, specify one or more crops, and request a valuation. A yield impact for the crops for soil type, slope, and/or other factors can be determined. Using the yield impact of the characteristics of the field, yield can be estimated, and by assuming a crop price, revenue for the field can be estimated. Land valuation can then reflect the estimated revenue.

Land valuation can also reflect other factors, such as an estimated cost of farming a piece of land. For example, a first field may be capable of obtaining a higher yield than a second field, but achieving the higher yield on the first field may be sufficiently more expensive (e.g. different types of fertilizer due to different soil type, etc.) than farming the second field that the second field is more profitable to farm. The second farm is therefore assigned a higher land valuation.

Risk can also be evaluated by land valuation tool 508. Some fields may have high potential or high average yield, but may have higher expected variability than others. One factor that can cause such variability is weather. One field may have very consistent weather, whereas another may be more prone to extreme weather events that can substantially depress yield. Analysis of historical weather data can be used to quantify these risk profiles. Certain soil types may also have higher risks for crop failure. Regardless of the various factors contributing to risk, risk is a factor that contributes to a field's long-term value. High expected yield variability or a high estimated risk of poor crop performance can adversely affect a field's value. The magnitude of the adverse effect on valuation can be tuned to the risk tolerance of the user requesting the valuation.

A seed finder 510 is configured to receive a request for determination of a seed variety for planting in a farm field. The request includes at least one of location information for the farm field or soil type information for the farm field. Seed finder 510 is further configured to provide a seed variety recommendation for planting in the farm field based on aggregated crop data and the seed variety request. In some examples, seed finder 510 is further configured to determine one or more highest-yielding seed varieties corresponding to the request based on the aggregated crop data. A seed variety recommendation can comprise at least one of the one or more highest-yielding seed varieties. Seed finder 510 can also be configured to receive the request for determination of a seed variety through a web portal.

Although farmers often desire to increase yield, seed finder 510 can also identify seed varieties that provide increased or "best available" performance with respect to other variables in addition to or in place of yield (seed varieties that, e.g., have the fastest relative maturity, require the least irrigation, require the least pesticide and/or fertilizer application, require the fewest man-hours of labor between planting and harvest, provide the highest profitability, etc.). In such cases, data can be aggregated according to the desired variables. For example, field-level data summaries for individual fields can include the relative maturity, irrigation, pesticide/fertilizer input, labor hours, etc. associated with the different seed varieties in the individual field, and these values can be averaged or otherwise combined across all fields in a region or across an agronomic network. This combined data can then be used to determine a seed variety that results in a desired value for a variable (e.g., the seed variety of a crop that requires the least irrigation, the seed variety of a crop that requires the least irrigation for a specific soil type, the crop and/or seed variety with the fastest relative maturity for a soil type and/or climate, etc.). A seed finder implementing such functionality can provide an option to select a variable for "optimization." As used herein, optimization does not necessarily imply a result that is an optimal or best solution but rather refers to a best available of a fixed number of choices or a better choice relative to other choices. In some examples, yield is the default variable, and a plurality of other variables can be selected by the user in place of or in addition to yield.

Yield analyzer 500, including yield driver module 502, yield impact module 504, yield explorer 506, land valuation tool 508, and seed finder 510, uses agronomic analytics to determine the impact of various yield factors on yield. The agronomic analytics can include both statistical approaches and machine learning approaches. Machine learning approaches, including "random forests" and "support vector machines" can be used to help automatically identify patterns in data that are useful for describing variability in yield. Statistical approaches, including linear models, generalized linear models, generalized linear mixed models, and generalized additive models, can, for example, then be applied to study those patterns in more detail and to quantify and uncover the underlying agronomic reasons for the patterns identified through the machine learning approaches.

The agronomic analytics can detect nonlinear relationships in data. Advanced statistical modeling approaches such as generalized additive models can be used to detect and quantify relationships between variables that are nonlinear. For example, the relationship between seed density and yield is typically nonlinear—if a farmer plants too few seeds, then yield tends to be lower than can be achieved with more seeds, but if the farmer plants too many, then the seeds tend to crowd each other and yield falls off.

The agronomic analytics also provide the ability to quantify and control the amount of spatial correlation in the data. Statistical models often assume that different observations in data are independent. However, this is often not the case in agricultural data because data are collected at spatially tagged locations. Data from nearby locations tends to be more similar, due in part, for example, to the fact that nearby locations have more similar soil and weather conditions than locations far away. Accounting for spatial correlation in the data enhances the validity of inferences from statistical models.

The agronomic analytics can also consider interactions between the various factors that may impact yield (or another variable of interest). Interactions occur, for example, when the contribution of one factor to yield differs based on the value of another factor (e.g. seeding rate has a certain impact on yield when seed variety A is planted, but has a different impact on yield when seed variety B is planted). Incorporating interactions into agronomic analytics allows the analytics to be more specifically tailored to the specific set of conditions on a particular field.

Variables that are included in various analytical models can be selected through domain knowledge and agronomic research. For example, based on previous knowledge and research, factors that are likely to influence crop yield can be determined.

Feature selection algorithms (such as sequential forward feature selection, where factors are added one-by-one to the model based on what factor most improves the model) can be used to identify factors that should be included in a model.

Attribution of variation in yield (or other variable of interest) to the various factors that are included in the model can be determined by examining the variability in the data to assess the magnitude of change in yield that is typically observed when different factors are changed. For example, if yield is highly sensitive to relatively small changes in a factor, that factor will have a high relative contribution to yield variability, whereas a factor that is associated with only modest changes in yield even when the factor is changed significantly will have a low relative contribution to yield variability.

Potential confounding variables can be included in statistical models so that the relationship between the factors of interest and yield can be assessed. For example, in an analysis of the impact of seeding rate on yield, a weather variable such as cumulative precipitation may be a confounding variable that is controlled for when probing the seeding rate-yield relationship. "Controlling" for a confounding factor means that the relationship between other factors and yield is quantified after statistically removing the effect of the confounding factor. Data can also be preprocessed or cleansed to remove unrealistic data before corrupting models.

In a specific set of examples, the agronomic analytics can involve extracting, from a database or other storage, data that is relevant to analysis of interest (e.g. data for a specific crop, crop-state combination, variety, variety-soil texture-state combination, etc.). A "response variable" of interest can then be selected. The response variable is the variable whose variability is being explained (e.g., yield, a measure of crop quality, crop production cost, pest or disease incidence, or other factor).

"Predictor variables" thought to be associated with variability in the response variable can also be identified. Predictor variables are the variables whose association with variability in the response variable is to be assessed and quantified. Example predictor variables include information about planting (e.g. planting speed), environmental conditions (e.g. soil type), weather (e.g. precipitation during the growing season), farming practices (e.g. tillage type), and others.

Additional predictor variables can include features that may not be explicitly of interest but that may explain variability in the response variable and therefore are included in the model in order to control for potentially confounding factors and enable more sound inferences about the predictor variables of interest. Such confounding factors may include field ID, farm ID, farmer ID, state/county/region in which the field is located, latitude, longitude, and year in which the crop was grown.

Candidate predictor variables can be selected by using domain knowledge, user input, data availability, machine learning analysis, or other methods. For examples in which machine learning analysis is used (e.g. a random forest or other tree-based modeling approach), the machine learning model can be fit using all (or a subset) of the candidate predictor variables. Diagnostics can be performed on the machine learning model to identify the predictor variables that best explained variability in the response variable. For example, in a random forest, a measure of predictor variable "importance" can be computed using information about how frequently each predictor variable was selected during the model fitting procedure. The results of these diagnostics can be used to reduce the number of predictor variables to be used in subsequent statistical modeling, restricting to the set of variables that best explain response variable variability in the machine learning analysis. The variables included in the set of variables can be determined based on a certain number of variables (e.g. 5, 10) or based on the variables necessary to explain a particular percentage of variability (e.g. 90%, 95%) in the response variable.

A statistical modeling procedure can be selected that quantifies the association between the identified predictor variables and response variable. The nature of the model selected can depend on the nature of relationship between predictors and response that is expected based on domain knowledge (which can be obtained by talking to farmers, experts in the field, or from published research). For example, if a linear relationship is expected, a linear model can be selected. In a nonlinear relationship is expected, higher-order terms (such as power transformations of the data) can be included in the model, or an approach that explicitly detects and quantifies nonlinear patterns, such as a generalized additive model, can be employed. The modeling approach selected also can depend on the nature of the response variable, and the expected probabilistic distribution of that variable (conditional on the values of the predictor variables). If, for example, the response variable is continuous and a Gaussian distribution is expected, a linear model with Gaussian response variable may be selected. If the response variable is discrete, models with Bernoulli (e.g. logistic regression, a type of generalized linear model), binomial, or Poisson response variable distributions can be selected. In some cases, several modeling procedures may be identified, implemented, and compared.

For some modeling approaches, assumptions are made about the distribution of the response variable, conditional on the values of the predictor variables (e.g. for linear models, a Gaussian distribution may be assumed). Other assumptions that can be made include the "Conditional Independence Assumption:" that is, that, given the values of all predictor variables included in the model, 1) the determination of the value or level of any particular predictor variable of interest and 2) the distribution of possible values of the response variable, are independent. This assumption implicitly asserts that "confounding variables" are either not associated with the response variable or have been included as predictor variables in the model. This allows the assumption that the model estimates the true relationship between a predictor variable of interest and the response variable without the risk of detecting a spurious correlation between a predictor variable and the response that results from that predictor variable being correlated with another, unaccounted-for predictor variable that in fact causes changes in the response variable.

Other assumptions that can be made include that: 1) all/most of the observations being used to fit the model are independent; 2) the observations are not spatially autocorrelated; 3) spatial autocorrelation has been explained by the other predictor variables included in the model (e.g. a smoothed two-dimensional spline on latitude and longitude in a generalized additive model); 4) spatial autocorrelation has been included in the error structure of the model (e.g. a generalized least squares model); and/or 5) a spatial auto-correlation-generating process has been explicitly included in the model (e.g. using a conditional autoregressive or simultaneous autoregressive model).

Real-world farm data can contain missing values, i.e. situations where certain data is not collected or not available for all records. In this case, various missing value imputation strategies can be employed before analysis. Example strategies include imputing data from similar observations, mean imputation, mode imputation, or median imputation.

Models as discussed above can be fit using statistical software. Parallel computing technologies can be employed to speed up the model fitting. Diagnostics can be used to assess quality of the model fit. The diagnostics used can depend on the nature of the model. Example diagnostics can include: 1) the percentage of variability in the response variable that was explained by the model; 2) the correlation between model-predicted values of the response variable and actual values of the response variable; 3) the range of the confidence intervals computed using the fit model (e.g the model can be used to compute a 95% confidence interval for the plausible range of the response variable for specified values of the predictor variables); 4) criteria that assess model quality, e.g. Akaike information criterion (AIC) or Bayesian information criterion (BIC), that quantify the tradeoff between how well the model fits the data and the model's complexity; 5) the distribution of errors obtained through a cross-validation procedure in which: the dataset is split into multiple groups, the model is fit using data from only a subset of those groups, the model is used to make predictions of the response variable for the subset of data not used to fit the model, and the deviations between those predictions and the true values are calculated (e.g. 10-fold cross validation, leave-one-out cross validation).

Further diagnostics can be performed to validate any assumptions made. For example, if the distribution of the response variable was assumed to be Gaussian, diagnostics can be performed to assess whether or not the distribution of model errors matches expectations that should hold true if that assumption is valid, i.e. that the errors also follow a Gaussian distribution. If spatial autocorrelation was assumed to be not present in the model or accounted for by the model, then diagnostics (e.g. Moran's I test) may be applied to the model errors to ensure that there is not a significant degree of spatial autocorrelation in those errors. The model structure of variables included in the model can be changed based on a detection of violation of assumptions in order to craft a model that does conform to assumptions (and therefore can be employed to provide statistically valid inferences).

Using model assessment criteria and assumption diagnostics, e.g. those described above, a model (e.g., a "best" model), or perhaps an ensemble (i.e. a group) of best models, can be selected. The criteria used to select a best model or ensemble of best models may vary based on user input and intended application of the model results, but can include selecting the model with the lowest average prediction error, lowest variance in prediction errors, or lowest probability of extreme errors (as defined by some user-specified threshold in prediction errors).

Once a model or ensemble of models has been selected, the model(s) can be used to extract the estimated relationship between a particular predictor variable of interest (the "focal" predictor variable) and the response variable. A range of values of the focal predictor variable can be specified (e.g. planting speed of two, three, four, five, etc. per hour), and values for the other predictor variables in the model (if any) can be set to constant values, e.g. their mean, median, or mode across the agronomic network, or user-specified values that match those most similar to the conditions on that particular user's farm. The values of the response variable predicted by the model can then be computed for each value of the focal predictor variable, each time using the constant values selected for all non-focal predictor variables. Confidence intervals specifying ranges of plausible values for the response variable under a specified level of statistical confidence (e.g. 80%, 90%, 95%) can also be computed.

Estimated values of the response variable for different values of the focal predictor variable, can be communicated to end users through a variety of data visualization methods including tables, line graphs, bar graphs, and others.

Figure 6:
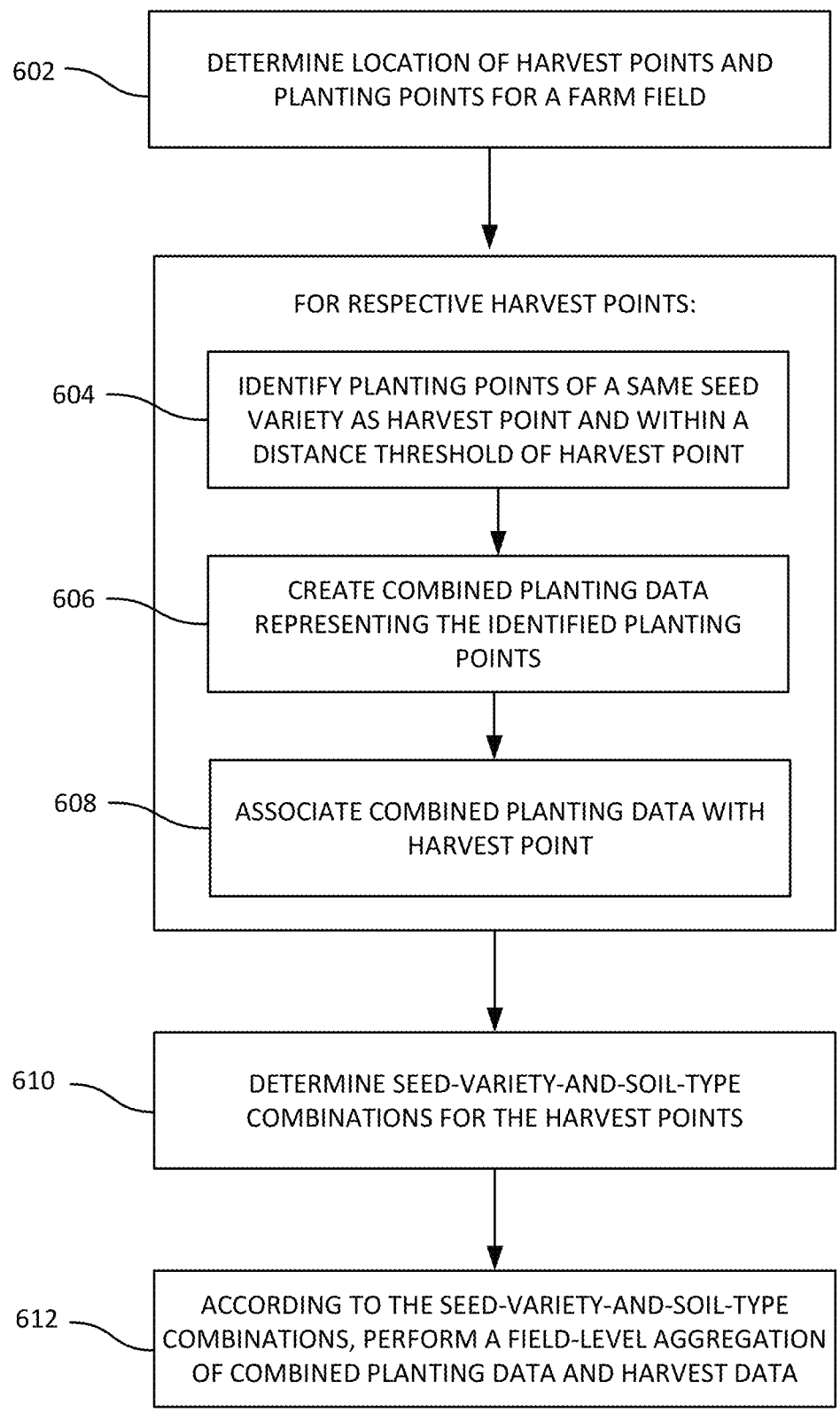
FIG. 6 illustrates an example method for creating a field-level data summary for a farm field.

FIGS. 6-9 illustrate various additional examples of functionality that can be, for example, performed by data integration module 410 of FIG. 4 or data integration module 312 of FIG. 3. FIG. 6 illustrates a method 600. In process block 602 of method 600, a location of (i) a plurality of harvest points and (ii) a plurality of planting points is determined for a farm field. The locations can be determined from latitude and longitude data provided with the harvest points and the planting points. The respective harvest points have associated harvest data, and the respective planting points have associated planting data. Process blocks 604, 606, and 608 are performed for the respective harvest points. In process block 604, a group of one or more of the plurality of planting points is identified that are (i) of a same seed variety as the harvest point and (ii) within a distance threshold from the harvest point. In process block 606, combined planting data is created for the group of planting points based on the planting data associated with individual planting points in the group of planting points. In some examples, combined planting data is created for a maximum number of planting points within the distance threshold from the harvest point. For example, combined planting data can be based on up to three, four, five, six, ten, or other number of planting points near the harvest point. The combined planting data is associated with the harvest point in process block 608. A soil type can also be associated with each harvest point.

Based on a soil type and a seed variety associated with the respective harvest points, seed-variety-and-soil-type combinations for the plurality of harvest points are determined in process block 610. According to the seed-variety-and-soil-type combinations, a field-level aggregation is performed, in process block 612, of both (i) the combined planting data associated with the respective harvest points and (ii) the harvest data associated with the respective harvest points. The field-level aggregation can create, for example, a field-level data summary. Weather information, crop rotation practice information, tillage information, and other information can be added to the field-level data summary prior to applying agronomic analytics. Field-level data summaries for many different farm fields can be analyzed and used to inform yield analyzer 414 of FIG. 4.

Figure 7:
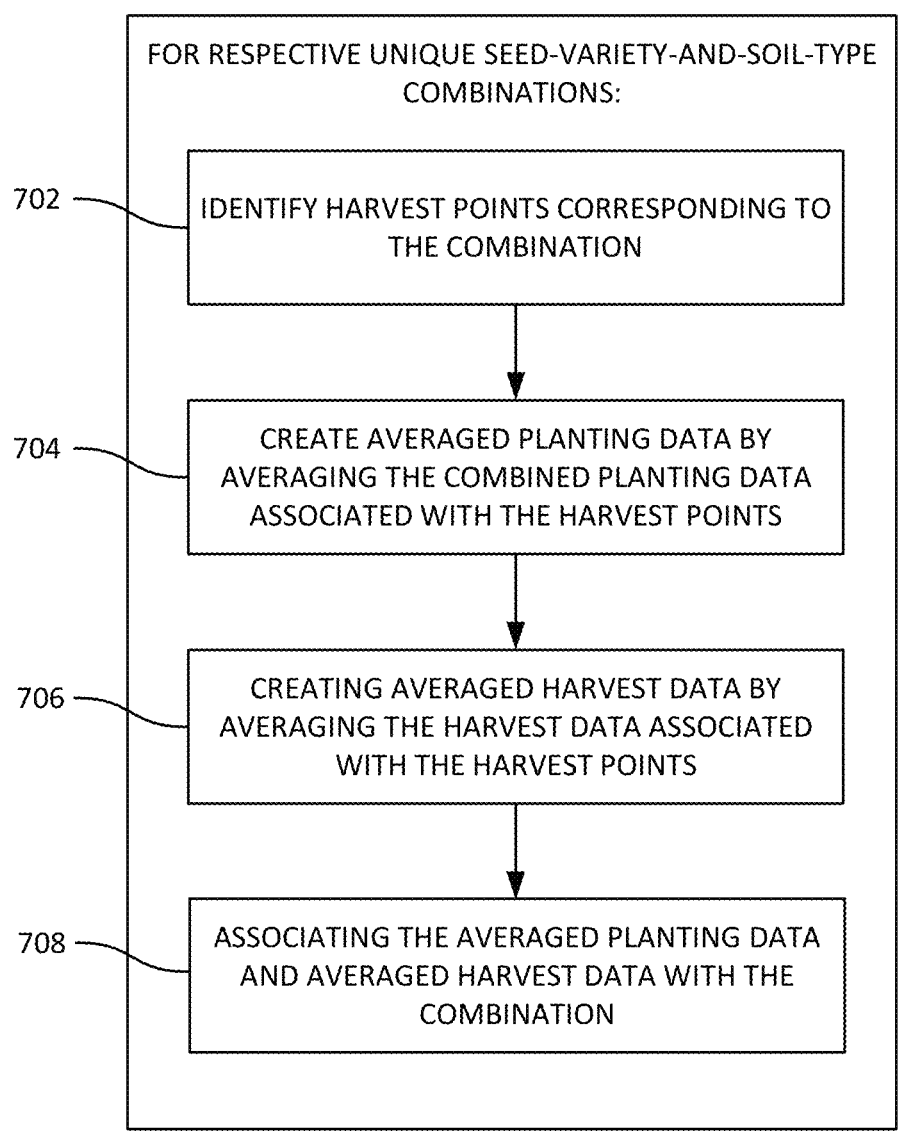
FIG. 7 illustrates an example method for creating a field-level data summary in which data is aggregated according to seed-variety-and-soil-type combinations.

FIG. 7 illustrates a method 700 of field-level aggregation for respective seed-variety-and-soil-type combinations. In process block 702, the harvest points of the plurality of harvest points corresponding to the seed-variety-and-soil-type combination are identified. In process block 704, averaged planting data is created by averaging the combined planting data associated with the harvest points. Averaged harvest data is created in process block 706 by averaging the harvest data associated with the harvest points. In process block 708, the averaged planting data and averaged harvest data are associated with the seed-variety-and-soil-type combination. Method 700 thus results in averaged planting data and averaged harvest data for each seed-variety-and-soil-type combination.

Figure 8:
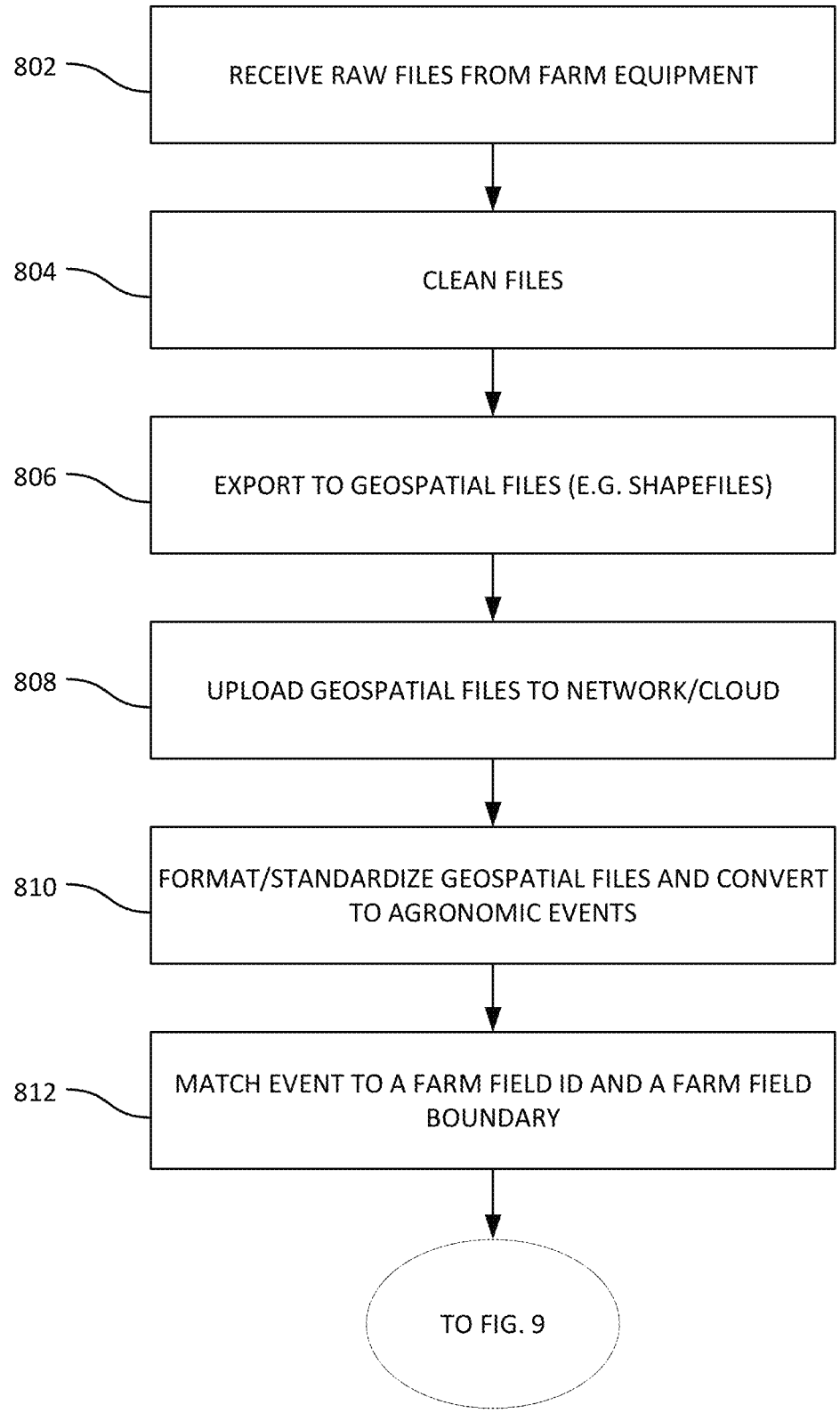
FIGS. 8 and 9 illustrate an example method for processing farmer data to inform yield analysis.
Figure 9:
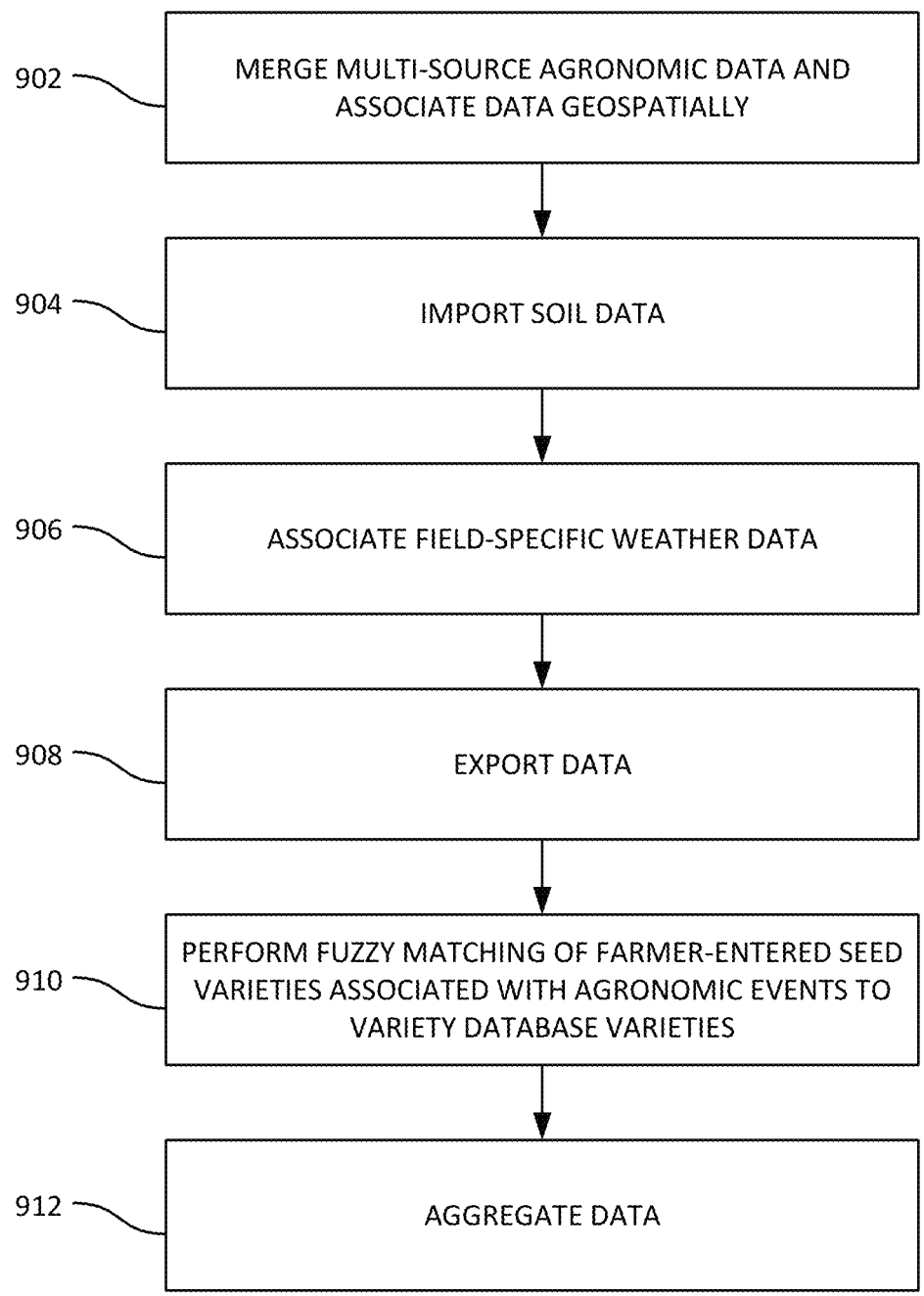

FIGS. 8 and 9 illustrate a detailed method 800 of processing farmer data to inform a yield analyzer such as yield analyzer 314 of FIG. 3 or yield analyzer 414 of FIG. 4. In process block 802, raw files are received. Raw files can be generated by planters or harvesters (e.g., monitors on planters or harvesters) and can be uploaded wirelessly or stored in memory on the planter or harvester for subsequent upload. Raw files can be uploaded via an agronomic web portal such as agronomic web portal 428 of FIG. 4.

In process block 804, the raw files are "cleaned" to remove, for example, unnecessary information, incorrect information, noisy data, or outlier data and/or to format the files for further processing. Process block 804 can be performed manually or through use of a software cleaning/formatting tool. In process block 806, the cleaned files are exported to geospatial files, such as shapefiles. In process block 808, the geospatial files are uploaded to a different location, such as a web services platform. In some examples, further processing of the geospatial files is performed without uploading the geospatial files to a different location or platform. In process block 810, the geospatial files are formatted and/or standardized and converted to agronomic "events."

As used herein, an agronomic event refers to data corresponding to operations performed on a farm field or portion of a farm field over a time period (e.g., day, days, weeks). For example, for a farm field, data associated with planting can be one event, and data associated with harvesting can be another event. Harvest data spanning several days can be considered a single event or multiple events. Harvest data for different fields or units of land, can be considered multiple events (e.g., an event corresponding to each unit of land). For specific units of land, harvest events can be associated with planting events, for example, as described herein. Additional events can be created manually and associated with other events. As an example, a tillage event can indicate when and how a farmer performed tillage on a particular field. The tillage event can be associated with the field-level data summaries that contain planting, harvest, and soil information. Other types of additional events include pest scouting events, crop damage events, irrigation events, etc.

In process block 812, agronomic events are each matched to a farm field identifier. In some examples, agronomic events are also matched to a farm field boundary corresponding to the farm field identifier. Farm field boundaries can be provided by farmers as a shapefile or other geospatial file or can be created using a tool, such as a web tool, in which a farmer can use touch, mouse, or other input to define the boundaries of a field on a displayed map. In process block 812, farm field identifier matches can be determined even if the data associated with the agronomic event and the correct farm field identifier is inconsistent or incomplete. For example, geospatial software can be used to perform a spatial intersection of planting and/or harvest points with field boundaries. An intersection threshold can be determined such that, for example, planting/harvest points are associated with a field when a minimum percentage of points are within the boundaries of the field.

Method 800 is continued in FIG. 9. In process block 902, multi-source agronomic data (e.g. planting data and harvest data) contained in the shapefiles uploaded in process block 808 is merged and associated geospatially. Process block 902 can include, for example, associating planting data and harvest data similarly to any of the examples described herein. Process block 902 can involve converting some or all of the data to a different cartographic projection, datum, and/or coordinate system. An example projection is universal transverse Mercator (UTM); an example datum is the North American Datum (NAD27 or NAD83); and an example coordinate system is the State Plane coordinate system used in the United States.

In process block 904, soil type data is imported and associated with the agronomic events. Soil type data can be SSURGO soil data or can be farmer-determined and/or farmer reported. In some examples, only general soil classifications are used, and in some examples, soil type is determined with more specificity (i.e., soil sub-types). In process block 906, field-specific weather data is associated with the agronomic events. The weather data can include, for example, precipitation data, severe weather events, temperature data, etc. The weather data can be, for example: data collected by a weather station on or near the farm field; data collected for cities or towns near the farm field; satellite imagery; radar data; gridded datasets produced by government agencies (e.g., the National Oceanic and Atmospheric Administration (NOAA)) that contain derived weather estimates based on aggregating weather station, satellite, radar, etc. data and performing modeling to integrate such data sources into estimates of weather for each grid cell; etc. An interpolation approach can be used to estimate field-specific weather conditions based on received weather data. After process block 906 is performed, the agronomic events include a variety of information about a farm field, including associated (and geospatially referenced) planting and harvest data, soil type data, and weather data. Other data can also be associated, such as farming practice data (e.g. fertilizer/pesticide applications, tillage status, crop rotation information, etc.).

In process block 908, the agronomic events are exported to, for example, cloud storage or web service storage such as Amazon Simple Storage Service (Amazon S3). Such storage can provide access from nearly any Internet connection as well as providing scalability. In process block 910, "fuzzy matching" of seed varieties associated with the agronomic events to seed varieties in a list of potential seed varieties is performed. In many instances, multiple names or variations of a name can be used for particular seed varieties. Additionally, farmers may only enter partial seed variety information into a planter, and/or the information entered by the farmer may not exactly match an "official" seed variety name. Process block 910 allows the names of seed varieties associated with the agronomic events to be effectively translated to a standard seed variety name to allow large-scale comparison and evaluation of data.

In some examples, before fuzzy matching is performed, domain knowledge is used to clean the text entered by a farmer to increase the likelihood of a successful match. In such a process, for example, the following types of information can be removed: brand information; genetic trait information; fertilizer/pesticide names for chemicals that have been applied concurrently; and planting population values. Common substitutions can also be performed based on a defined list of common errors/substitutions that can be updated as farmer data is received. For example, for a "P1234" seed variety, farmers might commonly enter "PI01234" or "PI1234." In this example, the "PI" or "PIO" can be replaced with "P."

When a seed variety that does not exactly match an entry in a list of possible seed varieties (e.g., a master seed list) is successfully matched via fuzzy matching (or even by manual intervention or follow-up with the farmer), the original entry can be saved and used to update the defined list of common errors/substitutions. In this way, once a particular non-conforming entry is matched, any future incidences of that non-conforming entry can be easily corrected. Matching of a farmer-entered seed variety to seed varieties in a master list can, in some instances, indicate multiple matches, including seed varieties of different crops. For example, a farmer-entered seed variety can be matched to both a soybean seed variety and a corn seed variety. Various heuristics (e.g., based on the yield of the crop) can then be used to determine a most likely crop type.

In process block 912, agronomic events are aggregated at a field-level. For example, data contained in the agronomic events can be aggregated by unique soil-type-and-seed-variety combinations. Examples of field-level aggregation are discussed, for example, with respect to FIGS. 6 and 7.

Agronomic analytics can be used to establish relationships between various factors and crop yield using the field-level aggregated data. For example, based on the field-level aggregated data for a large number of farm fields, statistical models can be used to determine the relative contribution of factors (e.g., seed variety, precipitation, soil type, row spacing, planting speed, fertilizer application, etc.) to yield. Agronomic analytics are discussed above in detail with respect to FIG. 5.

Various tools (e.g., a yield driver module, a yield impact module, a yield explorer, a land valuation tool, or a seed finder) can be informed by agronomic analytics and can be implemented, for example through a web portal. Aspects of example agronomic web portals are illustrated with respect to FIGS. 10-12.

FIG. 10 illustrates an agronomic web portal 1000. Agronomic web portal 1000 can be presented through a browser window as illustrated in FIG. 10. The functionality of agronomic web portal 1000 can also be provided through an application or "app" that connects to online resources via the Internet. Agronomic web portal 1000 can include a variety of resources, including "add field" functionality 1002 and "field manager" functionality 1004. Add field functionality 1002 provides a variety of ways for a farmer to add a field to the farmer's account. FIG. 10 shows "upload geospatial file" option 1006, "draw boundaries option" 1008, and "define boundaries using planting or harvest data" option 1010. Using option 1006, a farmer can upload a geospatial file, such as a shapefile, that defines the boundaries of a farm field. Add field functionality 1002 can reproject or convert the geospatial file to a standard projection and/or coordinate system. Using option 1008 a farmer can use touch, mouse, hover or other input to define a field's boundaries on a map background. Using option 1010, the latitude and longitude of planting (or harvest) points can be identified, and a field boundary encompassing the planting points can be generated. Other ways of providing field information are also contemplated.

Map 1012 provides a graphic of an added field's boundaries overlaid on a map background. A field can contain soil of multiple soil types. In some examples, a farmer can define subsections of different soil types within the field. For example, map 1012 includes field subsection 1014 and field subsection 1016, which have different soil types but are part of a same field. Map 1012 can also illustrate other fields associated with the farmer's account. For example, in map 1012, fields 1018 and 1020 are also associated with the farmer's account. In some examples, when a farmer logs in to his or her account, map 1012 displays the most recently added field, a zoomed-out map displaying all of the farmer's fields that have been added, or a user-defined group of fields.

Field manager functionality 1004 allows farmers to add data corresponding to fields in their profile (e.g. planting data, harvest data, fertilizer/pesticide application data, irrigation data, till status, etc.). Farmers can select a field using the field selector interface 1022 and can add data ("events") using an event interface 1024.

FIG. 11 illustrates other aspects of an agronomic web portal. A "Yield Analysis" interface 1102 provides users access to functionality similar to the various described examples. Yield Analysis interface 1102 can be used by a farmer to access yield drivers (an example is shown in interface 1102), yield impacts, yield explorer functionality, land valuation functionality, and/or seed finder functionality. In some examples, various additional interfaces are provided, such as "Analyze My Operation" interface 1104 and "Seed Finder" interface 1106. Analyze My Operation interface 1104 indicates how a particular field, farm, or group of farms or fields (e.g., fields associated with a farmer's account) have performed relative to different benchmarks. For example, FIG. 11 shows how a farm has performed compared to other farms in the state, county, and over all farms for which an agronomic analytics system (network) has data. Benchmarking is also possible on a country-wide, continent-wide, word-wide, etc. basis. Analyze My Operation interface 1104 can also allow farmers to see the various yield analyses described herein based on data specific to the farmer's field. That is, the impact of yield factors on yield for the farmer's fields can be determined and presented.

Seed Finder interface 1106 allows a user to select a field and receive a seed variety recommendation specific to the field. The seed variety recommendation can include one or more highest-yielding seed varieties for the characteristics of the field (e.g., soil type). Although Analyze My Operation interface 1104 and Seed Finder interface 1106 appear separately from Yield Analysis interface 1102 in FIG. 11, the functionality accessed through interfaces 1104 and 1106 can also be accessible through Yield Analysis interface 1102 and can be considered to be a subset of yield analysis functionality.

FIG. 12 illustrates an example Yield Analysis interface 1200. A user can select yield analysis interface 1102 of FIG. 11, for example, and be presented with yield analysis interface 1200. Yield analysis interface 1200 provides a crop selection control 1202 (indicating "corn") and a state selector 1204 (indicating "all"). Yield drivers information 1206, planting speed yield impact plot 1208, seeding rate yield impact plot 1210, and temperature at planting yield impact plot 1212 can be presented in response to the selections made through crop selection control 1202 and state selector 1204.

Yield drivers information 1206 indicates that for corn grown in all states for which the agronomic network has farm field data, the variation in yield among fields is 53% accounted for by seed variety, 10% by soil type, 7% by growing season precipitation, 1% by planting speed, and 27% by other factors. Factors that fall into "other factors" can be predetermined or user specified and can also be adjusted as data indicates that certain factors play a larger role in yield variation. "Other factors" can also be unknown or unexplained factors. That is, 5% of variation being accounted for other factors can indicate that the 5% variation in yield is unaccounted for. In some examples, a threshold (e.g., 1%, 5%, etc. contribution to yield variability) is used to determine whether a yield factor is included in "other factors" or listed separately.

Planting speed yield impact plot 1208 illustrates the change in yield (in bushels/acre) for different values of planting speed (in mph). Yield impact plot 1208 indicates both an estimated average value (curve in the middle of the shaded area, beginning at −5.0) and a percent confidence interval within which the average value can be expected to vary based on the agronomic analytics. For example, the bounded area around the middle curve can represent a 95% or other percent confidence interval. Yield impact plot 1208 indicates that for planting speeds between approximately 3.7 mph and approximately 5.7 mph, the planting speed that results in the highest increase in yield is approximately 5.0 mph. Yield impact plots 1210 and 1212 convey similar information regarding seeding rates and temperature at planting, respectively.

Farmers can use the information contained in yield drivers information 1206 to focus resources on a yield factor that is responsible for a greater variability in yield. For example, selecting a high-yielding seed variety (53% contribution to yield variability) for the soil type or other characteristics of a farmer's field is estimated to have a higher impact on yield than finding a planting speed (1% contribution to yield variability) that provides the largest increase in yield (as illustrated by yield impact plot 1208). Yield impact plots 1208, 1210, and 1212 allow farmers to determine values for a yield factor (e.g., planting speed, seeding rate, etc.) that corresponds to a highest available yield increase. Farmers can then alter their farming practices to conform to these yield factor values to realize an increase in yield. In some examples, the information presented in yield drivers information 1206 and yield impact plots 1208, 1210, and 1212 is presented in the form of a farmer recommendation to focus on one or more farming practices. In yield analysis interface 1200, three yield impact plots are shown. In some examples, yield impact plots are shown for a predetermined number of yield factors (e.g., a top two, three, or four yield factors that contribute the most to yield variability when other yield factors are controlled for). In some examples, farmers can specify yield factors for which to view yield impact plots. In this way, farmers can gather information regarding factors that, for example, can easily be altered (planting speed, seeding rate, etc.).

Figure 13:
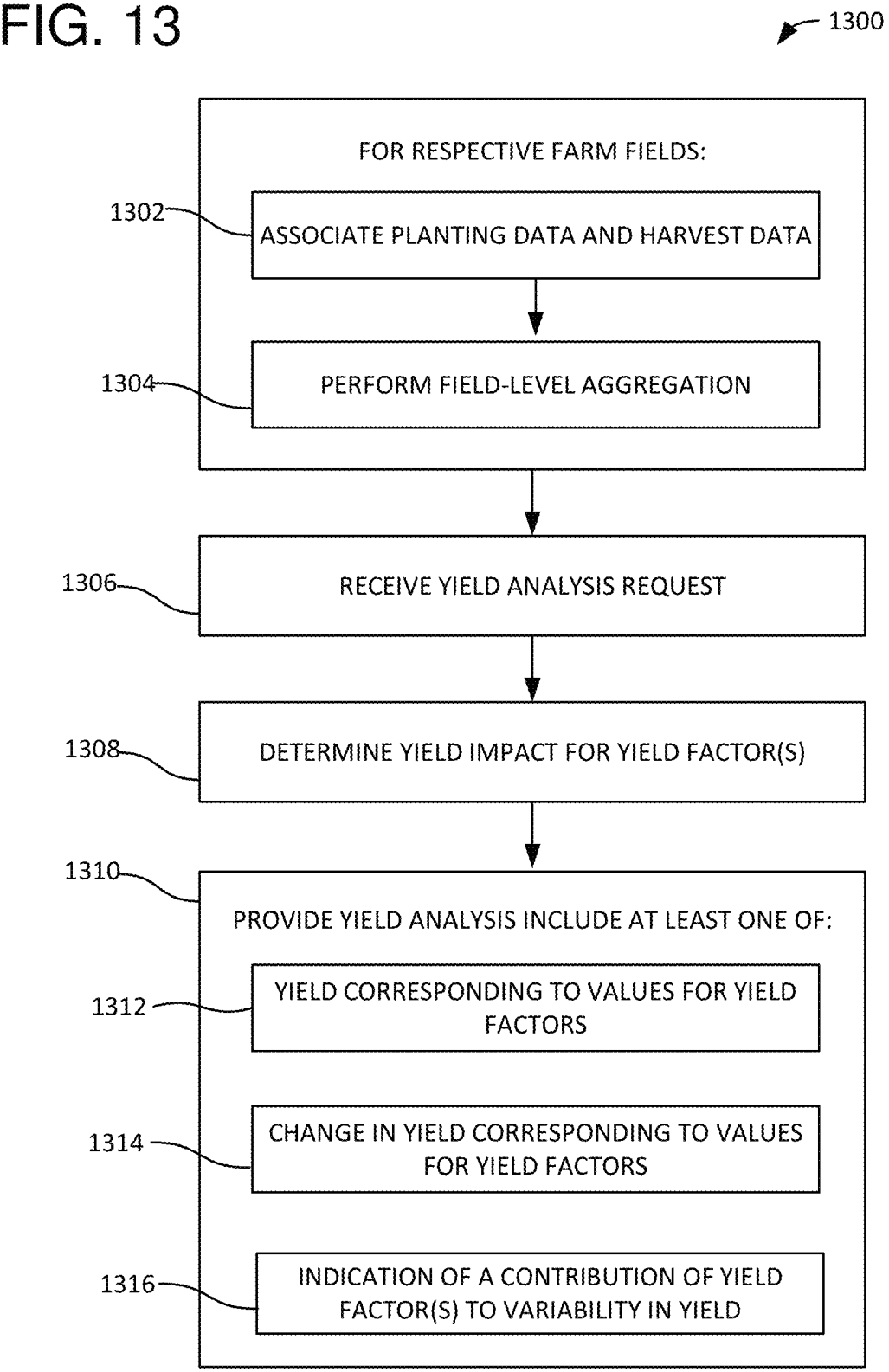
FIG. 13 illustrates an example method of providing a yield analysis.

An additional example method 1300 is illustrated in FIG. 13. Process blocks 1302 and 1304 are performed for respective farm fields of a plurality of farm fields. In process block 1302, planting data and harvest data for the farm field are associated based on locations of a plurality of planting points relative to locations of a plurality of harvest points. Soil type data based on the harvest points' location can also be identified and associated. In process block 1304, a field-level aggregation of planting data and harvest data is performed according to seed-variety-and-soil-type combinations. Field-level weather information can then be associated with the aggregated planting and harvest data. In process block 1306, a yield analysis request is received. Based on the field-level aggregations for the respective farm fields, in process block 1308, a yield impact of one or more yield factors is determined.

A yield analysis is provided in process block 1310 based on the determined yield impact of the one or more yield factors. The yield analysis can include at least one of aspects 1312, 1314, or 1316. Aspect 1312 of the yield analysis includes a yield corresponding to values for the one or more yield factors. Aspect 1314 of the yield analysis includes a change in yield corresponding to values for the one or more yield factors. Aspect 1316 of the yield analysis includes an indication of a contribution of at least one of the one or more yield factors to yield (e.g., a contribution to the variability in yield when controlling for the contributions of other yield factors).

In some examples, for the respective farm fields, weather data and soil-type data are also associated with the planting data and harvest data prior to the field-level aggregation. In some examples, the yield analysis request received in process block 1306 includes one or more seed varieties and planting data for a farm field in which seeds have been planted but for which crops have not yet been harvested. In some such examples, the yield analysis provided in process block 1310 can be based on a yield impact of at least one of the following yield factors: irrigation, fertilizer application, pesticide application, or weather events.

The described examples deliver more accurate and more targeted agronomic information to users, resulting in greater yield, less consumption of resources, and the like.

In practice, the systems shown herein can vary in complexity, with additional functionality, more complex components, and the like. For example, additional components can be included to implement security, redundancy, load balancing, report design, single sign on, and the like.

The systems described herein can be implemented in conjunction with any of the hardware components described herein, such as the computing systems described below (e.g., processing units, memory, and the like). In any of the examples herein, inputs, outputs, databases, and the like can be stored in one or more computer-readable storage media or computer-readable storage devices. The technologies described herein can be generic to the specifics of operating systems or hardware and can be applied in any variety of environments to take advantage of the described features.

Any of the methods described herein can be performed by computer-executable instructions (e.g., that when executed cause a computing system to perform the method) stored in one or more computer-readable media (e.g., storage or other tangible media) or stored in one or more computer-readable storage devices.

Example Computing Environments

Figure 14:
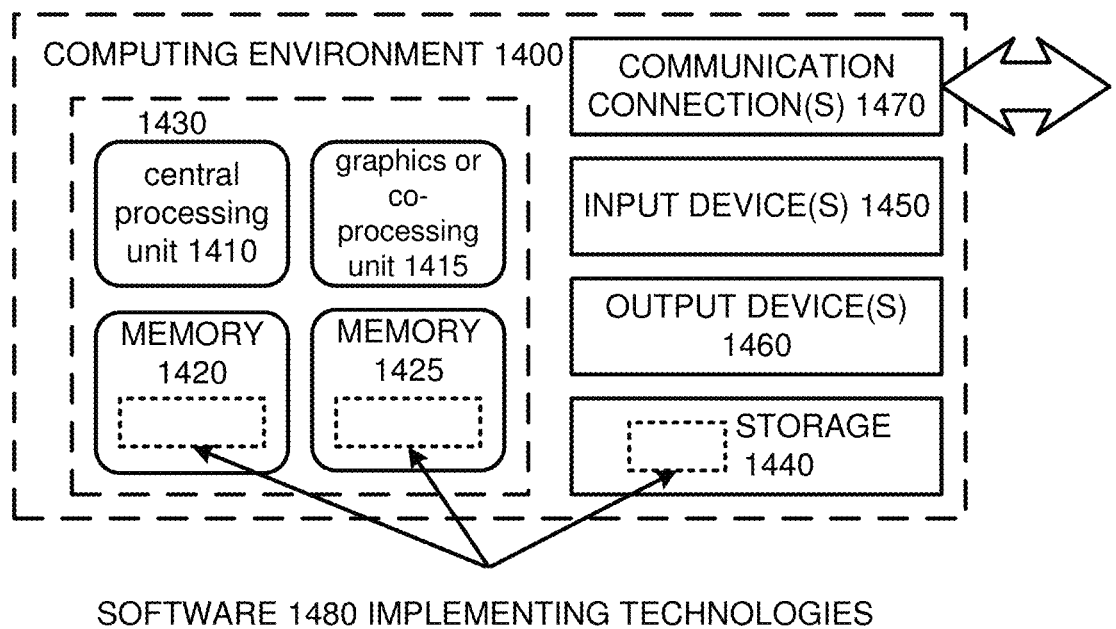
FIG. 14 illustrates an example computing environment in which some of the described examples can be implemented.

FIG. 14 illustrates a generalized example of a suitable computing system 1400 in which several of the described examples may be implemented. The computing system 1400 is not intended to suggest any limitation as to scope of use or functionality, as the described examples may be implemented in diverse general-purpose or special-purpose computing systems.

With reference to FIG. 14, the computing system 1400 includes one or more processing units 1410, 1415 and memory 1420, 1425. In FIG. 14, this basic configuration 1400 is included within a dashed line. The processing units 1410, 1415 execute computer-executable instructions. A processing unit can be a general-purpose central processing unit (CPU), processor in an application-specific integrated circuit (ASIC) or any other type of processor. In a multi-processing system, multiple processing units execute computer-executable instructions to increase processing power. For example, FIG. 14 shows a central processing unit 1410 as well as a graphics processing unit or co-processing unit 1415. The tangible memory 1420, 1425 may be volatile memory (e.g., registers, cache, RAM), non-volatile memory (e.g., ROM, EEPROM, flash memory, etc.), or some combination of the two, accessible by the processing unit(s). The memory 1420, 1425 stores software 1480 implementing one or more innovations described herein, in the form of computer-executable instructions suitable for execution by the processing unit(s). For example, memory 1420, 1425 can store farm data module 304, data integration module 312, and/or yield analyzer 314 of FIG. 3 or the corresponding components of FIG. 4.

A computing system may have additional features. For example, the computing system 1400 includes storage 1440, one or more input devices 1450, one or more output devices 1460, and one or more communication connections 1470. An interconnection mechanism (not shown) such as a bus, controller, or network interconnects the components of the computing system 1400. Typically, operating system software (not shown) provides an operating environment for other software executing in the computing system 1400, and coordinates activities of the components of the computing system 1400.

The tangible storage 1440 may be removable or non-removable, and includes magnetic disks, magnetic tapes or cassettes, CD-ROMs, DVDs, or any other medium which can be used to store information in a non-transitory way and which can be accessed within the computing system 1400. The storage 1440 stores instructions for the software 1480 implementing one or more innovations described herein. For example, storage 1440 can store farm data module 304, data integration module 312, and/or seed finder 314 of FIG. 3 or the corresponding components of FIG. 4.

The input device(s) 1450 may be a touch input device such as a keyboard, mouse, pen, or trackball, a voice input device, a scanning device, or another device that provides input to the computing system 1400. For video encoding, the input device(s) 1450 may be a camera, video card, TV tuner card, or similar device that accepts video input in analog or digital form, or a CD-ROM or CD-RW that reads video samples into the computing system 1400. The output device(s) 1460 may be a display, printer, speaker, CD-writer, or another device that provides output from the computing system 1400.

The communication connection(s) 1470 enable communication over a communication medium to another computing entity. The communication medium conveys information such as computer-executable instructions, audio or video input or output, or other data in a modulated data signal. A modulated data signal is a signal that has one or more of its characteristics set or changed in such a manner as to encode information in the signal. By way of example, and not limitation, communication media can use an electrical, optical, RF, or other carrier.

The innovations can be described in the general context of computer-executable instructions, such as those included in program modules, being executed in a computing system on a target real or virtual processor. Generally, program modules include routines, programs, libraries, objects, classes, components, data structures, etc. that perform particular tasks or implement particular abstract data types. The functionality of the program modules may be combined or split between program modules as desired in various embodiments. Computer-executable instructions for program modules may be executed within a local or distributed computing system.

For the sake of presentation, the detailed description uses terms like "determine" and "use" to describe computer operations in a computing system. These terms are high-level abstractions for operations performed by a computer, and should not be confused with acts performed by a human being. The actual computer operations corresponding to these terms vary depending on implementation.

Example Cloud-Supported Environments

Figure 15:
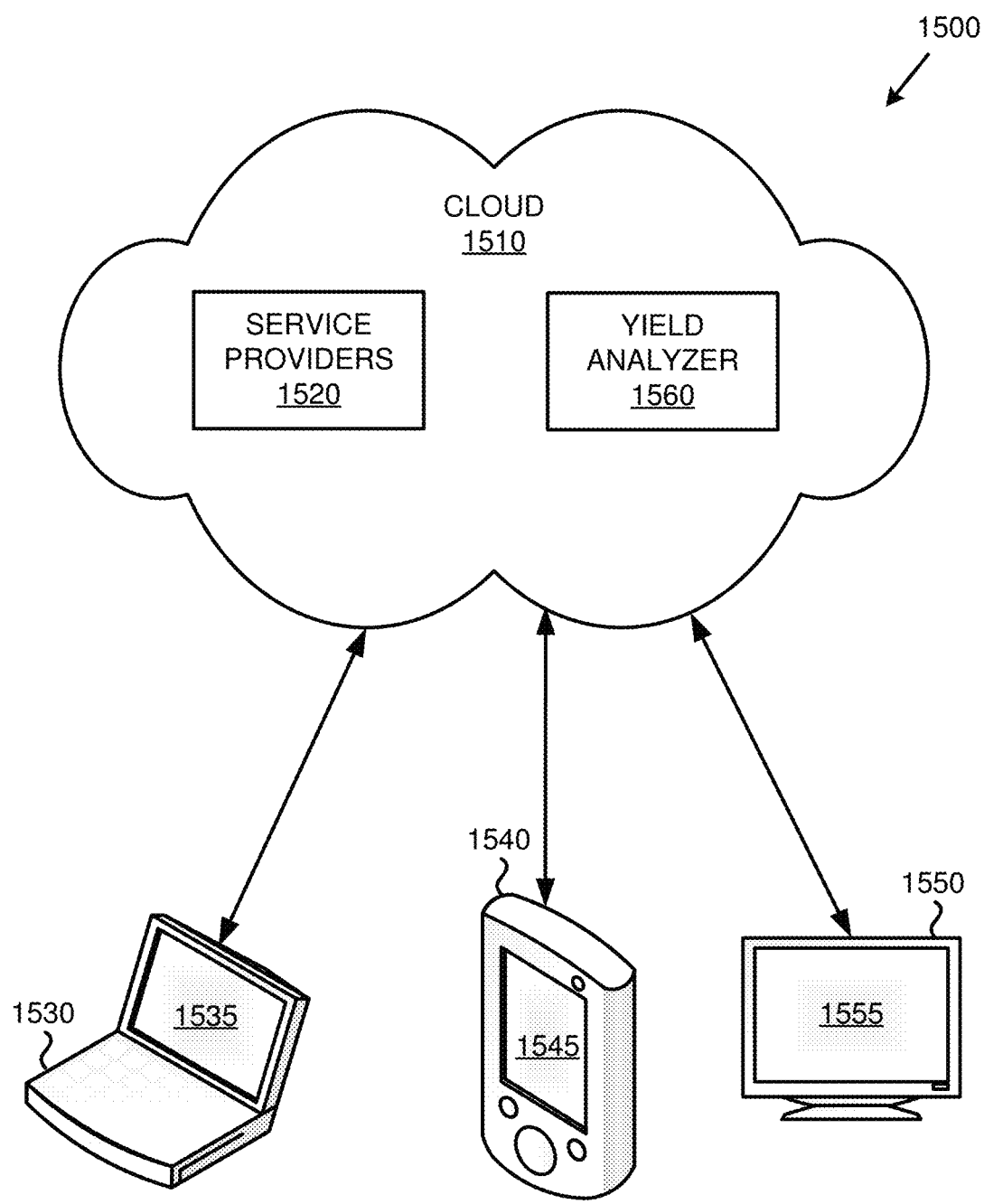
FIG. 15 illustrates an example computing environment in which some of the described examples can be implemented.

In example environment 1500 of FIG. 15, the cloud 1510 provides services for connected devices 1530, 1540, 1550 with a variety of screen capabilities. Connected device 1530 represents a device with a computer screen 1535 (e.g., a mid-size screen). For example, connected device 1530 could be a personal computer such as desktop computer, laptop, notebook, netbook, or the like. Connected device 1540 represents a device with a mobile device screen 1545 (e.g., a small size screen). For example, connected device 1540 could be a mobile phone, smart phone, personal digital assistant, tablet computer, and the like. Connected device 1550 represents a device with a large screen 1555. For example, connected device 1550 could be a television screen (e.g., a smart television) or another device connected to a television (e.g., a set-top box or gaming console) or the like. One or more of the connected devices 1530, 1540, 1550 can include touch screen capabilities. Touchscreens can accept input in different ways. For example, capacitive touchscreens detect touch input when an object (e.g., a fingertip or stylus) distorts or interrupts an electrical current running across the surface. As another example, touchscreens can use optical sensors to detect touch input when beams from the optical sensors are interrupted. Physical contact with the surface of the screen is not necessary for input to be detected by some touchscreens. Devices without screen capabilities also can be used in example environment 1500. For example, the cloud 1510 can provide services for one or more computers (e.g., server computers) without displays.

Services can be provided by the cloud 1510 through service providers 1520, or through other providers of online services (not depicted). For example, cloud services can be customized to the screen size, display capability, and/or touch screen capability of a particular connected device (e.g., connected devices 1530, 1540, 1550).

In example environment 1500, the cloud 1510 provides the technologies and solutions described herein to the various connected devices 1530, 1540, 1550 using, at least in part, the service providers 1520. For example, the service providers 1520 can provide a centralized solution for various cloud-based services. The service providers 1520 can manage service subscriptions for users and/or devices (e.g., for the connected devices 1530, 1540, 1550 and/or their respective users). Cloud 1510 can provide, for example, yield analyzer 1560.

Example Computer-Readable Media

Any of the computer-readable media herein can be non-transitory (e.g., volatile memory such as DRAM or SRAM, nonvolatile memory such as magnetic storage, optical storage, or the like) and/or tangible. Any of the storing actions described herein can be implemented by storing in one or more computer-readable media (e.g., computer-readable storage media or other tangible media). Any of the things (e.g., data created and used during implementation) described as stored can be stored in one or more computer-readable media (e.g., computer-readable storage media or other tangible media). Computer-readable media can be limited to implementations not consisting of a signal.

Alternatives

Any of the methods described herein can be implemented by computer-executable instructions in (e.g., stored on, encoded on, or the like) one or more computer-readable media (e.g., computer-readable storage media or other tangible media) or one or more computer-readable storage devices (e.g., memory, magnetic storage, optical storage, or the like). Such instructions can cause a computing device to perform the method. The technologies described herein can be implemented in a variety of programming languages.

The technologies from any example can be combined with the technologies described in any one or more of the other examples. In view of the many possible embodiments to which the principles of the disclosed technology may be applied, it should be recognized that the illustrated embodiments are examples of the disclosed technology and should not be taken as a limitation on the scope of the disclosed technology. Rather, the scope of the disclosed technology includes what is covered by the following claims. We therefore claim as our invention all that comes within the scope and spirit of the claims.

We claim:

1. One or more non-transitory computer-readable media storing computer-executable instructions for:

receiving a yield analysis request for a crop type;

based on aggregated crop data, determining, for the crop type, a yield impact of one or more yield factors, wherein:

the one or more yield factors comprises seed variety, the aggregated crop data is based on planting data and harvest data for a plurality of farm fields, wherein at least some of the planting data and harvest data are acquired using sensors mounted to farming machinery, and the aggregated crop data is determined in part by associating planting data and harvest data for respective farm fields of the plurality of farm fields, wherein the planting data and the harvest data for respective farm fields are associated by:

determining locations of a plurality of harvest points; and for the respective harvest points:

identifying one or more planting points that are within a distance threshold from the harvest point;

creating combined planting data for the one or more planting points within the distance threshold, wherein creating the combined planting data comprises determining a weighted average of at least some planting data for the one or more planting points based on a distance of the respective planting points from the harvest point; and associating the combined planting data with the harvest point; and providing a yield analysis for the crop type, the yield analysis based on the yield impact of the one or more yield factors; and providing a seed variety recommendation.

2. The one or more non-transitory computer-readable media of claim 1, wherein the one or more yield factors further comprise at least one of: soil type, precipitation, planting speed, row spacing, seed spacing, seeding rate, planting depth, crop rotation, tillage, irrigation, fertilizer application, pesticide application, or weather events.

3. The one or more non-transitory computer-readable media of claim 1, wherein the yield impact comprises at least one of (i) a yield corresponding to values for the one or more yield factors or (ii) a change in yield corresponding to values for the one or more yield factors.

4. The one or more non-transitory computer-readable media of claim 1, wherein the yield analysis comprises an indication of the yield impact of a yield factor.

5. The one or more non-transitory computer-readable media of claim 4, wherein the indication of the yield impact of the yield factor comprises a graphical representation depicting a change in yield corresponding to values for the yield factor.

6. The one or more non-transitory computer-readable media of claim 1, wherein the yield analysis comprises an indication of a contribution of one or more yield factors to yield.

7. The one or more non-transitory computer-readable media of claim 6, wherein the indication of a contribution of one or more yield factors to yield comprises, for the respective yield factors, an indication of the individual contribution of the yield factor to variability in yield when other yield factors are controlled for.

8. The one or more non-transitory computer-readable media of claim 1, wherein the aggregated crop data are aggregated by combinations of soil type and seed variety, and wherein the aggregated crop data comprises soil data and weather data.

9. At least one computing device comprising a processor and a memory, the computing device implementing a system, the system comprising:
a farm data module configured to receive farm field information, planting data, and harvest data for a plurality of farm fields;
a data integration module configured to create, for respective farm fields of the plurality of farm fields, a field-level data summary representing the physical growth of one or more crops on the farm field, the field-level data summary created by associating planting data and harvest data for the farm field, wherein:
at least some of the planting data and harvest data are acquired using sensors mounted to farming machinery, and
the associating the planting data and the harvest data comprises:
determining a latitude and a longitude for a plurality of harvest points in the harvest data;
determining a latitude and a longitude for a plurality of planting points in the planting data; and
for the respective harvest points:
identifying one or more of the plurality of planting points that are (i) of a same seed variety as a harvest point and (ii) within a distance threshold from the harvest point;
creating combined planting data for the one or more planting points within the distance threshold; and
associating the combined planting data with the harvest point; and
a yield analyzer configured to:
receive a yield analysis request for a crop type;
based on the field-level data summaries, determine crop-specific yield impacts of one or more yield factors, wherein the one or more yield factors comprises seed variety
based on the crop-specific yield impacts of the one or more yield factors, provide a yield analysis for the crop type; and
provide a seed variety recommendation.

10. The at least one computing device of claim 9, wherein the yield analyzer is further configured to provide a recommendation of at least one of: a planting practice, a fertilizer application practice, a pesticide application practice, or an irrigation practice.

11. The at least one computing device of claim 9, wherein the yield analysis comprises at least one of:
yield corresponding to values for the one or more yield factors;
change in yield corresponding to values for the one or more yield factors; or
an indication of a contribution of at least one of the one or more yield factors to yield.

12. The at least one computing device of claim 9, wherein the data integration module is configured to create a respective field-level data summary by:
associating a soil type with the respective harvest points of a plurality of harvest points in the harvest data;
for a plurality of harvest points in the harvest data, determining combinations of (i) associated seed variety and (ii) associated soil type; and
for the respective combinations:
identifying harvest points associated with the combination;
combining at least some of the planting data and harvest data associated with the identified harvest points.

13. The at least one computing device of claim 9, wherein the yield analyzer is further configured to receive the request for the yield analysis through a web portal.

14. A computer-implemented method, comprising:
for respective farm fields of a plurality of farm fields:
associating planting data and harvest data for the farm field based on locations of a plurality of planting points relative to locations of a plurality of harvest points, wherein the planting data and the harvest data for respective farm fields are associated by:
determining locations of a plurality of harvest points; and
for the respective harvest points:
identifying one or more planting points that are within a distance threshold from the harvest point;
creating combined planting data for the one or more planting points within the distance threshold, wherein creating the combined planting data comprises determining a weighted average of at least some planting data for the one or more planting points based on a distance of the respective planting points from the harvest point; and
associating the combined planting data with the harvest point; and
performing a field-level aggregation of planting data and harvest data according to seed-variety-and-soil-type combinations, wherein at least some of the planting data and harvest data are acquired using sensors mounted to farming machinery;
receiving a yield analysis request;
based on the field-level aggregations for the respective farm fields, determining a yield impact of one or more yield factors, wherein the one or more yield factors comprises seed variety; and
providing a yield analysis based on the determined yield impact of the one or more yield factors, the yield analysis including at least one of:
yield corresponding to values for the one or more yield factors;
change in yield corresponding to values for the one or more yield factors; or
an indication of a contribution of at least one of the one or more yield factors to yield; and
providing a seed variety recommendation.

15. The computer-implemented method of claim 14, wherein for the respective farm fields, weather data and soil-type data are also associated with the planting data and harvest data prior to the field-level aggregation.

16. The computer-implemented method of claim 14, wherein the yield analysis request includes one or more seed varieties and planting data for a farm field in which seeds have been planted but for which crops have not yet been harvested, and wherein the yield analysis is based on a yield impact of at least one of the following yield factors: irrigation, fertilizer application, pesticide application, or weather events.

17. The one or more non-transitory computer-readable media of claim 1, further comprising instructions for:
- based on the yield analysis, transmitting a farming practice instruction to a computing device associated with farm equipment, wherein the farming practice instruction comprises an update to settings or values of the farm equipment.

18. The one or more non-transitory computer-readable media of claim 17, further comprising instructions for:
- updating the farm equipment with the updated settings or values, wherein the farm equipment operates according to the updated settings or values.

19. The method of claim 14, wherein the seed variety recommendation comprises one or more highest-yielding seed varieties, and further comprising altering farming practices to conform to the seed variety recommendation.

* * * * *